(12) United States Patent
DeLuca et al.

(10) Patent No.: US 9,452,177 B2
(45) Date of Patent: Sep. 27, 2016

(54) VITAMIN D COMPOUNDS AND METHODS FOR REDUCING OCULAR HYPERTENSION (OHT)

(75) Inventors: Hector F. DeLuca, Deerfield, WI (US); Galina D. Kutuzova, Madison, WI (US); Paul L. Kaufman, Madison, WI (US); B'Ann True Gabelt, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 436 days.

(21) Appl. No.: 12/921,497

(22) PCT Filed: Mar. 10, 2009

(86) PCT No.: PCT/US2009/036679
§ 371 (c)(1),
(2), (4) Date: Nov. 22, 2010

(87) PCT Pub. No.: WO2009/114540
PCT Pub. Date: Sep. 17, 2009

(65) Prior Publication Data
US 2011/0059926 A1 Mar. 10, 2011

Related U.S. Application Data

(60) Provisional application No. 61/035,192, filed on Mar. 10, 2008.

(51) Int. Cl.
| *A61K 31/59* | (2006.01) |
| *A61K 31/593* | (2006.01) |
| *A61K 9/00* | (2006.01) |
| *A61K 31/592* | (2006.01) |

(52) U.S. Cl.
CPC ............ *A61K 31/59* (2013.01); *A61K 9/0048* (2013.01); *A61K 31/592* (2013.01); *A61K 31/593* (2013.01)

(58) Field of Classification Search
CPC ... A61K 31/59; A61K 31/592; A61K 31/593
See application file for complete search history.

(56) References Cited

U.S. PATENT DOCUMENTS

| 5,876,709 | A * | 3/1999 | Itoh et al. .................. 424/78.04 |
| 6,248,732 | B1 | 6/2001 | Itoh et al. |
| 6,706,725 | B1 | 3/2004 | Bernardon et al. |
| 2005/0065133 | A1 | 3/2005 | Lee et al. |
| 2006/0258726 | A1 | 11/2006 | Billot et al. |
| 2007/0099879 | A1 | 5/2007 | Sheibani et al. |
| 2007/0225377 | A1 | 9/2007 | Flatt et al. |

FOREIGN PATENT DOCUMENTS

| JP | 10158171 | 6/1998 |
| WO | 0185194 A1 | 11/2001 |
| WO | 2007117563 A2 | 10/2007 |

OTHER PUBLICATIONS

Riley, et al., ATPases of Ciliary Epithelium: Cellular and Subcellular Distribution and Probable Role in Secretion of Aqueous Humor, Experimental Eye Research, 1986, 42(6):559-568.
Rozsa, et al., Gene Expression Profile of Human Trabecular Meshwork Cells in Response to Long-Term Dexamethasone Exposure, Molecular Vision, 2006, 12:125-141.
Scott, et al., Comparative Studies Between Species that Do and Do Not Exhibit the Washout Effect, Experimental Eye Research, 2007, 84(3):435-443.
Shevde, et al., A Potent Analog of 1a,25-dihydroxyvitamin D3 Selectively Induces Bone Formation, Proc. Natl. Acad. Sci. USA, 2002, 99(21):13487-13491.
Suda, et al., Biological Activity of 25-Hydroxyergocalciferol in Rats, J. Nutrition, 1970, 100:1049-1052.
Supuran, Carbonic Anyhdrases: Novel Therapeutic Applications for Inhibitors and Activators, Nature Reviews Drug Discovery, 2008, 7:168-181.
Takamatsu, et al. Localization of Prostaglandin E Receptor Subtypes in the Ciliary Body of Mouse Eye, Experimental Eye Research, 2000, 70(5):623-628.
Tan, et al., Recent Developments in Understanding the Pathophysiology of Elevated Intraocular Pressure, Current Opinion in Ophthalmology, 2006, 17(2):168-174.
Ten Tusscher, et al., Peripheral Neural Circuits Regulating IOP? A Review of its Anatomical Backbone, Documenta Ophthalmologica, 1994, 87(4):291-313.
Tian, et al., The Role of the Actomyosin System in Regulating Trabecular Fluid Outflow, Experimental Eye Research, 2009, 88(4):713-717.
Trzeciakowski, Review: Central Control of Intraocular Pressure, Journal of Ocular Pharmacology, 1987, 3(4):367-378.
Vaajanen, et al., Does the Renin-Angiotensin System Also Regulate Intraocular Pressure?, Ann. Med., 2008, 40(6):418-427.
Vaajanen, et al., Is There a Relationship Between Blood Pressure and Intraocular Pressure? An Experimental Study in Hypertensive Rats, Current Eye Research, 2008, 33(4):325-332.
Vittitow, et al., Genes Expressed in the Human Trabecular Meshwork During Pressure-Induced Homeostatic Response, Journal of Cellular Physiology, 2004, 201(1):126-137.
Wallow, et al., Ocular Renin Angiotensin: EM Immunocytochemical Localization of Prorenin, Current Eye Research, 1993, 12(10):945-950.
Wang, et al., Effect of Flunarizine, a Calcium Channel Blocker, on Intraocular Pressure and Aqueous Humor Dynamics in Monkeys, Journal of Glaucoma, 2008, 17(1):73-78.
Wordinger, et al., Effects of TGF-B2, BMP-4, and Gremlin in the Trabecular Meshwork: Implications for Glaucoma, Investigative Ophthalmology & Visual Science, 2007, 48(3):1191-1200.
Zadshir, et al., The Prevalence of Hypovitaminosis D Among US Adults: Data from the NHANES III, Ethnicity & Disease, 2005, 15(Suppl 5):S5-97-S5-101.
Zhang, et al., Aquaporin Deletion in Mice Reduces Intraocular Pressure and Aqueous Fluid Production, J. Gen. Physiol., 2002, 119:561-569.

(Continued)

Primary Examiner — Zohreh Fay
(74) Attorney, Agent, or Firm — Quarles & Brady LLP

(57) ABSTRACT

The present invention relates to compounds and methods for reducing intraocular pressure and treating ocular hypertension in a subject.

9 Claims, 17 Drawing Sheets

(56) References Cited

OTHER PUBLICATIONS

Zimmerman, et al., Timolol, Arch. Ophthalmol., 1977, 95:601-604.
European Patent Office, Supplementary European Search Report, Application No. EP09719452.6, Aug. 8, 2011.
Applicant, Response to European Patent Office Search Report, Application No. EP09719452.6, Feb. 24, 2012.
Mexican Patent Office, Translation of the Requirements Stated by the Examiner in the Official Action, Application No. MX/a/2010/009814, 2012.
Applicant, Response to the Mexican Patent Office Official Action, Application No. MX/a/2010/009814, Apr. 19, 2012.
Database WPI, Week 199834, Thomson Scientific, AN1998-393391, XP002652804, Jun. 16, 1998.
International Search Report and Written Opinion as mailed on Jan. 12, 2010 for International Application No. PCT/US2009/036679.
Acott, et al., Extracellular Matrix in the Trabecular Meshwork, Experimental Eye Research, 2008, 86(4):543-561.
Armaly, et al., Biostatistical Analysis of the Collaborative Glaucoma Study, Arch. Ophthalmol., 1980, 98:2163-2171.
Barany, Simultaneous Measurement of Changing Intraocular Pressure and Outflow Facility in the Vervet Monkey by Constant Pressure Infusion, Investigative Ophthalmology, 1964, 3:135-143.
Chidlow, et al., The 5-HT1A Receptor Agonist 8-OH-DPAT Lowers Intraocular Pressure in Normotensive NZW Rabbits, Experimental Eye Research 1999, 69(6):587-593.
Chu, et al., Mechanisms and Sites of Ocular Action of 7-Hydroxy-2-Dipropylaminotetralin: A Dopamine3 Receptor Agonist, Journal of Pharmacoloy and Experimental Therapeutics, 2000, 293(3):710-716.
Clark, et al., Ophthalmic Drug Discovery, Nature Reviews Drug Discovery, 2003, 2:448-459.
Constad, et al., Use of an Angiotensin Converting Enzyme Inhibitor in Ocular Hypertension and Primary Open-Angle Glaucoma, American Journal of Ophthalmology, 1988, 105:674-677.
Costagliola, et al., Effect of Oral Captopril (SQ 14225) on Intraocular Pressure in Man, European Journal of Ophthalmology, 1995, 5:19-25.
Crawford, et al., Pilocarpine Antagonizes Prostaglandin F2a-Induced Ocular Hypotension in Monkeys, Arch. Ophthalmol., 1987, 105:1112-1116.
Croft, et al., Comparison of Goldmann Tonometry Measurements Using Creamer vs. Fluorescein in Cynomolgus Monkeys, Basic and Clinical Applications of Vision Science, 1997, 60:213-216.
Cullinane, et al., Renin-Angiotensin System Expression and Secretory Function in Cultured Human Ciliary Body Non-Pigmented Epithelium, Br. J. Ophthalmol., 2002, 86:676-683.
DeLuca, Overview of General Physiologic Features and Functions of Vitamin D1-4, Am. J. Clin. Nutr., 2004, 80 (suppl):1689S-1696S.
DeLuca, Evolution of Our Understanding of Vitamin D, Nutrition Reviews, 2008, 66(Suppl. 2):S73-S87.
Dismuke, et al., Ouabain-Induced Changes in Aqueous Humour Outflow Facility and Trabecular Meshwork Cytoskeleton, Br. J. Ophthalmol., 2009, 93:104-109.
Duggal, et al., Identification of Novel Genetic Loci for Intraocular Pressure, Arch. Ophthalmol., 2007, 125:74-79.
Eremeev, et al., A Thermoreversible Hydrogel Suspension Prolonging the Action of Proxodolol Eye Drops, Pharmaceutical Chemistry Journal, 2006, 40(1):36-39.
Gabelt, et al., H-7 Effect on Outflow Facility After Trabecular Obstruction Following Long-Term Echothiophate Treatment in Monkeys, Investigative Ophthalmology & Visual Science, 2004, 45(8):2732-2736.
Gabelt, et al., Apraclonidine and Brimonidine Effects on Anterior Ocular and Cardiovascular Physiology in Normal and Sympathectomized Monkeys, Experimental Eye Research, 1994, 59(6):633-644.
Guist, et al., Anwendung und Wirkungsweise der Hochdosierten Vitamin-D-Therapie Beim Glaukom, Klinische Monatsblatter fur Augenheilkunde, 1953, 123(5):555-568.
Halloran, et al., Intestinal Calcium Transport: Evidence for Two Distinct Mechanisms of Action of 1,25-Dihydroxyvitamin D3, Archives of Biochemistry and Biophysics, 1981, 208(2):477-486.
Harris, Vitamin D and African Americans, J. Nutr., 2006, 136:1126-1129.
Holick, The Vitamin D Deficiency Pandemic and Consequences for Nonskeletal Health: Mechanisms of Action, Molecular Aspects of Medicine, 2008, 29(6):361-368.
Jones, et al., Current Understanding of the Molecular Actions of Vitamin D, Physiological Reviews, 1998, 78(4):1193-1231.
Kanner, et al., Glaucoma Medications: Use and Safety in the Elderly Population, Drugs Aging, 2006, 23(4):321-332.
Kass, et al., The Ocular Hypertension Treatment Study, Arch. Ophthalmol., 2002, 120:701-713.
Kaufman, Aqueous Humor Outflow, Current Topics in Eye Research, 1984, 4:97-138.
Kaufman, Enhancing Trabecular Outflow by Disrupting the Actin Cytoskeleton, Increasing Uveoscleral Outflow with Prostaglandins, and Understanding the Pathophysiology of Presbyopia, Experimental Eye Research, 2008, 86(1):3-17.
Kaufman, et al., 'Minified' Goldmann Applanating Prism for Tonometry in Monkeys and Humans, Arch. Ophthalmol., 1980, 98:542-546.
Kaufman, et al., Future of IOP-Lowering Medication for Glaucoma Therapy, Glaucoma, Essentials in Ophthalmology, 2006, pp. 138-155.
Klein, et al., Intraocular Pressure and Systemic Blood Pressure: Longitudinal Perspective: The Beaver Dam Eye Study, Br. J. Ophthalmol., 2005, 89:284-287.
Kuespert, et al., CEACAMs: Their Role in Physiology and Pathophysiology, Current Opinion in Cell Biology, 2006, 18(5):565-571.
Kutuzova, et al., Gene Expression Profiles in Rat Intestine Identify Pathways for 1,25-Dihydroxyvitamin D3 Stimulated Calcium Absorption and Clarify Its Immunomodulatory Properties, Archives of Biochemistry and Biophysics, 2004, 432(2):152-166.
Kutuzova, 1,25-Dihydroxyvitamin D3 Regulates Genes Responsible for Detoxification in Intestine, Toxicology and Applied Pharmacology, 2007, 218(1):37-44.
Li, Vitamin D Regulation of the Renin-Angiotensin System, Journal of Cellular Biochemistry, 2003, 88(2):327-331.
Li, et al., Vitamin D: A Negative Endocrine Regulator of the Renin-Angiotensin System and Blood Pressure, Journal of Steroid Biochemistry and Molecular Biology, 2004, 89-90:387-392.
Libby, et al., Complex Genetics of Glaucoma Susceptibility, Annual Review of Genomics and Human Genetics, 2005, 6:15-44.
Lim, et al., Mechanism of Action of Bimatoprost, Latanoprost, and Travoprost in Healthy Subjects, A Crossover Study, Ophthalmology, 2008, 115(5):790-795.
Lukas, et al., Susceptibility to Glaucoma: Differential Comparison of the Astrocyte Transcriptome from Glaucomatous African American and Caucasian American Donors, Genome Biology, 2008, 9:R111.1-R111.19.
Maltese, et al., Pharmacokinetic Profile of Topical Flunarizine in Rabbit Eye and Plasma, Journal of Ocular Pharmacology and Therapeutics, 2003, 19(2):171-179.
Marquis, et al., Management of Glaucoma: Focus on Pharmacological Therapy, Drugs Aging, 2005, 22(1):1-21.
Miao, et al., Gene Expression and Functional Studies of the Optic Nerve Head Astrocyte Transcriptome from Normal African Americans and Caucasian Americans Donors, PLoS ONE, 2008, 3(8):e2847, 14 pages.
Mincione, et al., The Development of Topically Acting Carbonic Anhydrase Inhibitors as Antiglaucoma Agents, Current Topics in Medicinal Chemistry, 2007, 7(9):849-854.
Ontoso, et al., Does Medical Treatment of Mild Intraocular Hypertension Prevent Glaucoma?, European Journal of Epidemiology, 1997, 13(1):19-23.
Orihashi, et al., Potent Reduction of Intraocular Pressure by Nipradilol Plus Latanoprost in Ocular Hypertensive Rabbits, Biol. Pharm. Bull., 2005, 28(1):65-68.

(56) References Cited

OTHER PUBLICATIONS

Piltz, et al., Contralateral Effect of Topical B-Adrenergic Antagonists in Initial One-Eyed Trials in the Ocular Hypertension Treatment Study, Am. J. Ophthalmol., 2000, 130(4):441-453.

Pintor, Adenine Nucleotides and Dinucleotides as New Substances for the Treatment of Ocular Hypertension and Glaucoma, Curr. Opin. Investig. Drugs, 2005, 6(1):76-80.

Podos, et al., Experimental Compounds to Lower Intraocular Pressure, Australian and New Zealand Journal of Ophthalmology, 1989, 17:129-135.

Podos, et al., The Effect of Vanadate on Aqueous Humor Dynamics in Cynomolgus Monkeys, Invest. Ophthalmol. Vis. Sci., 1984, 25:359-361.

Rasmussen, et al., Aqueous Humor Dynamics in Monkeys in Response to the Kappa Opioid Agonist Bremazocine, Trans. Am. Ophthalmol. Soc., 2007, 105:225-239.

Reis, et al., Differences in Vitamin D Status as a Possible Contributor to the Racial Disparity in Peripheral Arterial Disease, Am J. Clin. Nutr., 2008, 88:1469-1477.

* cited by examiner

Mean (n=8) serum Ca2+ Level in monkeys after 5th topical application of a 6μg 2MD in 5μl propelene glycol in OS vs. 5ml propelene glycol in OD

VITAMIN D COMPOUNDS AND METHODS FOR REDUCING OCULAR HYPERTENSION (OHT)

CROSS-REFERENCE TO RELATED APPLICATIONS

This application claims priority to U.S. Provisional Application No. 61/035,192, filed Mar. 10, 2008, the entirety of which is hereby incorporated by reference for all purposes.

STATEMENT OF FEDERALLY SPONSORED RESEARCH

Not Applicable.

FIELD OF THE INVENTION

The present invention relates to compounds and methods for reducing intraocular pressure and treating ocular hypertension in a subject.

BACKGROUND OF THE INVENTION

Elevated intraocular pressure (IOP) is a component in at least two visual system disorders. The first disorder is primary open angle glaucoma (POAG), which combines elevated IOP with a progressive optic neuropathy and results in characteristic excavation of the optic nerve head and corresponding visual field defects. The second disorder is ocular hypertension (OHT), in which IOP is elevated but no glaucomatous damage to the optic nerve head is observed and the detectable visual field does not change. Elevated IOP is a critical risk factor in the development of glaucomatous optic neuropathy [Armaly, 1980] and other visual field disorders. For example, between 4% [Kass, 2002] and 20% [Ontoso, 1997] of people with OHT will develop visual field defects within five years.

Although elevated IOP is a component in POAG, some other forms of glaucoma do not involve elevated IOP. Normal tension glaucoma (NTG) is a clinical entity characterized by similar damage of the optic nerve head and similar visual field defects, but without an elevated IOP. POAG is arbitrarily distinguished from NTG using a cut-off point of IOP of 21 mmHg [Vass, 2007].

Ocular hypertension is the strongest known risk factor for POAG. Intraocular pressure (IOP) is determined by aqueous humor (AqH) production in the ciliary body and by AqH drainage through the trabecular meshwork (TM) and uveoscleral drainage pathways. Elevated IOP occurs as a result of increased resistance to drainage of AqH primarily through the conventional outflow system and is associated with the increased extracellular matrix (ECM) deposition and decreased cellularity [Clark, 2003].

However, the normal regulation of IOP and retinal ganglion cell function remains largely unknown. A general lack of knowledge exists regarding the cellular and biochemical mechanisms behind IOP and OHT, making it difficult to identify the molecular events responsible for OHT. There is little understanding of the genetics of POAG and even less knowledge of the cell biology underlying it [Tan, 2006].

The main goal of treatment for all forms of glaucoma is the preservation of visual function. The cornerstone of therapy to achieve this goal is the reduction of IOP. Lowering IOP remains the mainstay of therapy in the management of glaucoma, since it has been shown to be effective in reducing optic nerve damage and thus the loss of visual field [Kaufman, 2006]. All antiglaucoma drugs currently in clinical use could be classified into two categories according to their mechanism of action on aqueous flow dynamism. One is the group of drugs suppressing aqueous production ($\alpha$ and $\beta$-adrenergic blockers, carbonic anhydrases inhibitors and $Na^+/K^+$-ATPase inhibitors) and the other is the group promoting aqueous outflow either by enhancing the pressure-sensitive (presumed trabecular) outflow pathway (cholinergics, MMP activators and protein kinase inhibitors) or by increasing the pressure-insensitive (uveoscleral) outflow (prostaglandins) [Clark, 2003; Institute, 2006; Orihashi, 2005; Marquis, 2005]. The assessment of the amount of flow through each pathway depends upon the measurement technique [Lim, 2008].

Conventional treatments of OHT, IOP and/or glaucoma have relied on the use of small molecules acting at receptors or acting as mediators in signaling pathways to enhance aqueous humor outflow or decrease aqueous inflow in order to lower IOP. In the current pharmacological treatment of glaucoma, five major classes of medications are presently available for clinical use. These include $\alpha$-adrenergic agonists, $\beta$-adrenergic antagonists ($\beta$-blockers), carbonic anhydrase inhibitors (CAIs), cholinergics and prostaglandin (PG) compounds. The IOP is lowered either by decreasing the production of aqueous humor in the eye ($\alpha$- and $\beta$-adrenergic blockers, carbonic anhydrases inhibitors and $Na^+/K^+$-ATPase inhibitors) or by improving its outflow either through the conventional pathway (through the canal of Schlemm such as cholinergics, MMP activators and protein kinase inhibitors) or through the uveoscleral outflow pathway (PGs) [Clark, 2003; Institute, 2006; Orihashi, 2005; Marquis, 2005]. Over the course of time, most patients will use more than one medication, singly and in varying combinations, experimenting with differing classes of compounds with varying mechanisms of action. All of the above-mentioned treatment agents have one or more serious and undesirable side effects [Kaufman, 2006].

Therefore, a need exists for a new class of effective IOP-lowering compounds which have minimal or beneficial side effects. The search for new, more effective and more selective compounds with fewer side effects for the treatment of ocular hypertension and glaucoma may also contribute to understanding the molecular mechanisms involved in the regulation of intraocular pressure.

SUMMARY OF THE INVENTION

The present invention provides a method of reducing ocular hypertension in a subject, the method comprising administering to at least one eye a therapeutically effective amount of a vitamin D compound according to the following formula:

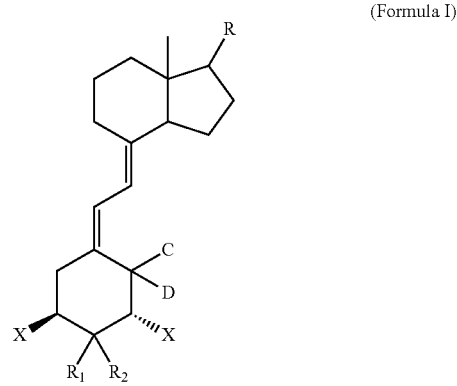

(Formula I)

wherein R is

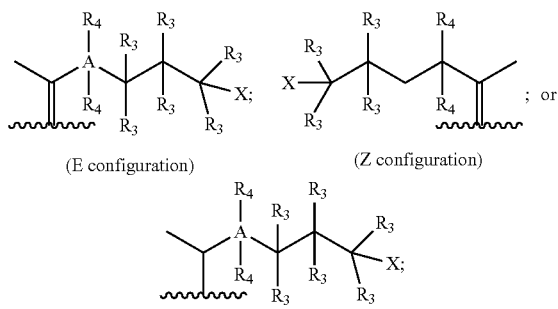

(E configuration)    (Z configuration)

wherein $R_1$ and $R_2$ are H, methyl or 3'-hydroxypropylidine, or taken together as =$CH_2$ or methylene; wherein $R_3$ and $R_4$ are selected from H, alkyl (1-3 carbons), alkoxy, and can be the same or different from each other; wherein X is a hydroxyl or protected hydroxyl group; wherein A is oxygen or carbon, with the proviso that if A is oxygen, then $R_4$ is absent; and wherein C and D are H or taken together as =$CH_2$; and wherein the intraocular pressure of the subject is reduced by at least 15%. The compound may be used to reduce intraocular pressure in one or both eyes of a subject, as well as a method of preventing glaucoma in a patient.

In a preferred version, the compound of the present invention is administered in an amount ranging from about 0.2 μg to about 1 mg per day as a topical preparation, such as eye drops.

In a further preferred version, the vitamin D compound is selected from the group consisting of 1α,25-dihydroxyvitamin $D_3$ (1,25-$(OH)_2D_3$); 2-methylene-19-nor-(20S)-1α,25-dihydroxyvitamin $D_3$; 1α,25-dihydroxy-19-nor-vitamin $D_2$; 2-(3'-hydroxypropylidene)-19-nor-1α,25-dihydroxyvitamin $D_3$ (E-isomer); 17-20 dehydro-2-methylene-19-nor-(20S)-1α,25-dihydroxyvitamin $D_3$ (E- and Z-isomers); 26-homo-1α,25-dihydroxyvitamin $D_3$; 26,27-Dimethyl-1α,25-dihydroxyvitamin $D_3$; or 25-hydroxyvitamin $D_3$.

A kit is also provided, comprising a compound according to Formula I, and instructions for use. The compounds and methods of the present invention provide many advantages. For instance, the compounds can be used to reduce ocular hypertension in both eyes while only treating one eye. Further, the compounds do not have the serious and unwanted side effects common in conventional ocular hypertension treatments. Further still, the compounds of the present invention are stable and easily formulated.

BRIEF DESCRIPTION OF THE DRAWINGS

FIG. 10 depicts the expression of representative genes modulated by vitamin D that are involved in the regulation of IOP (rat intestine data (filled bars), mouse calvarial cells data (open bars).

DETAILED DESCRIPTION OF THE INVENTION

I. In General

Figure 1:
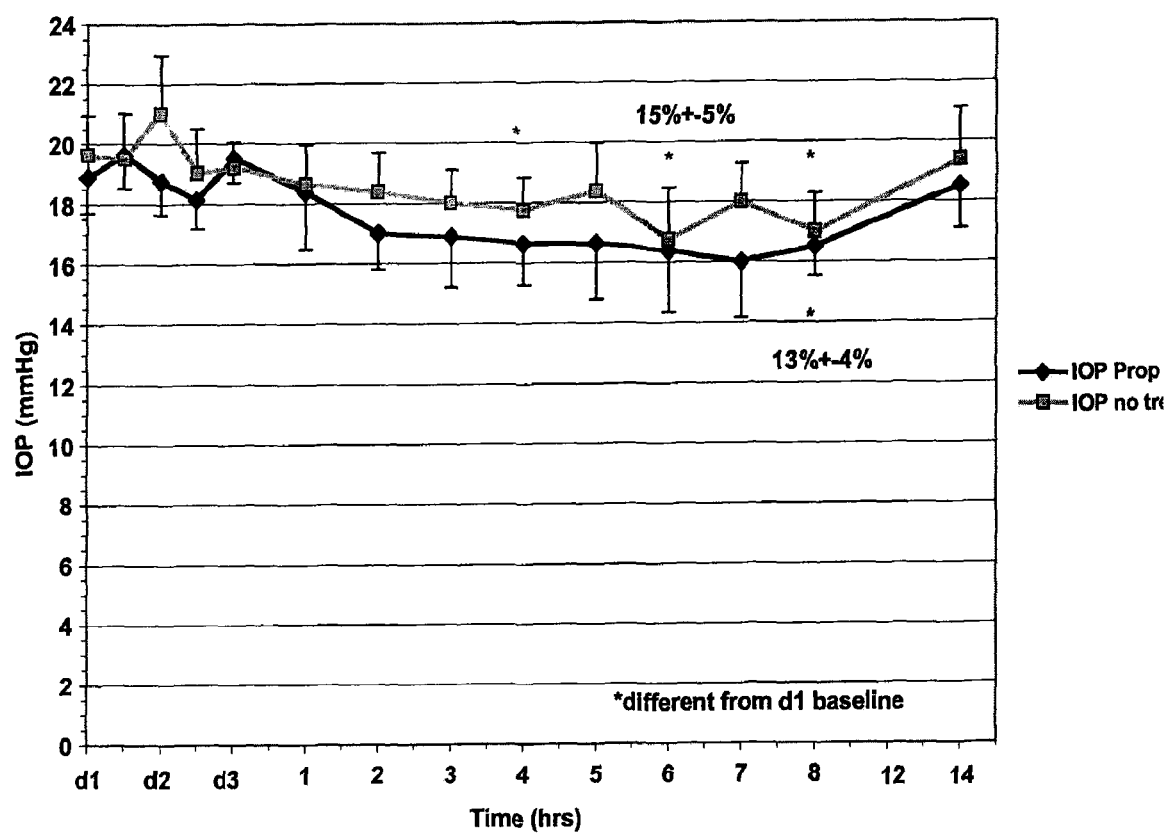
FIG. 1 depicts an IOP response (mean=8) after the 5th dose of twice daily treatments with 5 ul propylene glycol in one eye and non-treated opposite eye.

In the specification and in the claims, the terms "including" and "comprising" are open-ended terms and should be interpreted to mean "including, but not limited to . . . ." These terms encompass the more restrictive terms "consisting essentially of" and "consisting of."

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Abbreviations used for Vitamin D Compounds are as follows: PrGl represents Propylene Glycol; 1,25 represents $1\alpha,25$-dihydroxyvitamin $D_3$ ($1,25$-$(OH)_2D_3$); 2MD represents 2-methylene-19-nor-(20S)-$1\alpha,25$-dihydroxyvitamin $D_3$; AGR represents 2-(3'-hydroxypropylidene)-19-nor-$1\alpha$, 25-dihydroxyvitamin $D_3$ (E-isomer); BH represents 2-methylene-19-nor-(20S)-1-hydroxy-bishomopregnacalciferol (2MbisP); 20R-2MD represents 2-methylene-19-nor-(20R)-$1\alpha,25$-dihydroxyvitamin $D_3$; ZP represents $1\alpha,25$-dihydroxy-19-nor-vitamin $D_2$ (Zemplar or Paricalcitol); E or Z represents 17-20 dehydro-2-methylene-19-nor-(20S)-$1\alpha,25$-dihydroxyvitamin $D_3$ (E- or Z-isomers); 26-Homo represents 26-homo-$1\alpha,25$-dihydroxyvitamin $D_3$; 26,27-Diethyl represents 26,27-Dimethyl-$1\alpha,25$-dihydroxyvitamin $D_3$; $VitD_3$ represents Vitamin $D_3$; $1\alpha$-$(OH)D3$ represents $1\alpha$-hydroxyvitamin $D_3$; and $25(OH)D3$ represents 25-hydroxyvitamin $D_3$.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

II. The Invention

Since the beginning of the last century, vitamin D has been established as the primary regulator of calcium and phosphorous homeostasis in mammals and the major compound for prevention and treatment of rickets. Decades of research has revealed that vitamin D (its hormonal form, $1\alpha,25$-dihydroxyvitamin $D_3$ or $1,25$-$(OH)_2D_3$) is able to prevent and cure a broad spectrum of diseases including cancers, diabetes, autoimmune diseases, hypertension and more [DeLuca, 2008]. However, here we show for the first time that vitamin D ($1,25$-$(OH)_2D_3$) is a very powerful and promising compound for reducing ocular hypertension. As described below, unilateral topical application of vitamin D to the eye greatly reduces the intraocular pressure in both treated and control eyes, thus exhibiting an unprecedentedly strong bilateral hypotensive effect without changing the aqueous humor formation or drainage rates of the eye.

The present invention is a method of reducing ocular hypertension (OHT) in a patient, the method comprising administering to at least one eye of subject exhibiting an elevated ocular pressure in at least one eye a therapeutically effective amount of a vitamin D compound of the following formula:

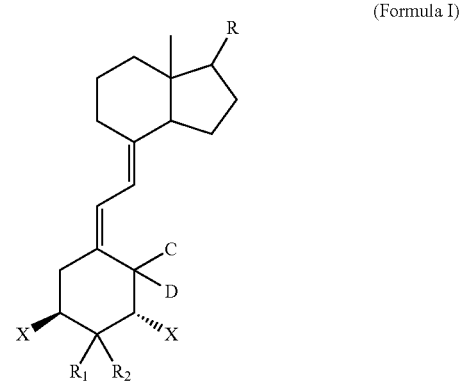

(Formula I)

wherein R is

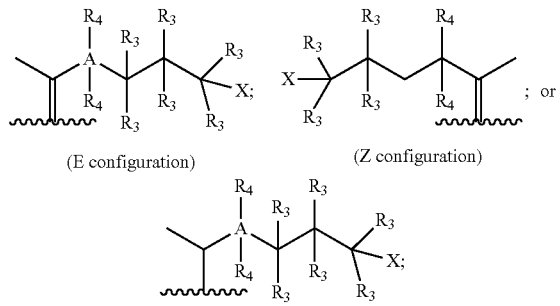

wherein $R_1$ and $R_2$ are H, methyl or 3'-hydroxypropylidine, or taken together as =$CH_2$ or methylene; wherein $R_3$ and $R_4$ are selected from H, alkyl (1-3 carbons), alkoxy, and can be the same or different from each other; wherein X is a hydroxyl or protected hydroxyl group; wherein A is oxygen or carbon, with the proviso that if A is oxygen, then $R_4$ is absent; and wherein C and D are H or taken together as =$CH_2$, wherein upon administration with the compound according to Formula I, the intraocular pressure is reduced, preferably by at least 15%.

By "ocular hypertension" we mean intraocular pressure that is consistently higher than normal, typically exceeding 21 mmHg.

By "reducing" we mean reducing the ocular hypertension of the subject by at least 5%, at least 10%, and preferably by at least 15% to 50% per eye.

By reducing the OHT in a subject, the compounds and methods of the present invention provide a novel treatment for glaucoma and other disorders exhibiting an elevated intraocular pressure. For purposes of the present invention, "treating" or "treatment" describes the management and care of a subject for the purpose of combating the disease, condition, or disorder. The terms embrace both preventative, i.e., prophylactic, and palliative treatment. Treating includes the administration of a compound of present invention to prevent the onset of the symptoms or complications, alleviating the symptoms or complications, or eliminating the disease, condition, or disorder.

In a preferred embodiment, one would evaluate the success of the treatment described above in several ways. Typically, one would measure the intraocular pressure of the affected eye or eyes and calculate a percentage OHT reduction [Kass, 2002]. By "measure" we mean determine the IOP ("tonometry") through any method known to the art, including but not limited to digital tonometry (Indentation method), Maklakov tonometer (Impression-Applanation Tonometry), Tonomat instrument (Impression-Applanation Tonometry), Wolfe Tonometer (Indentation tonometer), Goldmann Tonometry (Applanation Tonometry), and/or a non-contact tonometer (Indentation tonometry). Alternatively, one may directly measure changes in vision.

By "subject" we mean mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

By "administering" we mean any means for introducing a colchicines neoglycoside into the body, preferably into the systemic circulation. Examples include but are not limited to oral, buccal, sublingual, pulmonary, transdermal, transmucosal, as well as subcutaneous, intraperitoneal, intravenous, and intramuscular injection.

By "therapeutically effective amount" we mean amount of a compound that, when administered to a subject for treating a disease, is sufficient to effect such treatment for the disease. The "therapeutically effective amount" will vary depending on the compound, the disease state being treated, the severity or the disease treated, the age and relative health of the subject, the route and form of administration, the judgment of the attending medical or veterinary practitioner, and other factors. In a preferred embodiment, a therapeutically effective amount means an amount of vitamin D compound sufficient to reduce ocular hypertension between at least 10% and 50% in each eye. Reducing OHT by at least 20% will slow the progression of glaucoma in most patients suffering from glaucoma. Lowering OHT by at least 20% also produces a 50% protective benefit in patients with ocular hypertension but no optic disc or visual field deterioration [Kass, 2002; Kanner, 2006; National Eye Institute website at www.nei.nih.gov].

By "vitamin D compound" we mean any compound or derivative of the vitamin D formula described above, including 1α,25-dihydroxyvitamin $D_3$ (1,25-$(OH)_2D_3$); 2-methylene-19-nor-(20S)-1α,25-dihydroxyvitamin $D_3$ (E-isomer); 1α,25-dihydroxy-19-nor-vitamin $D_2$; 2-methylene-19-nor-(20S)-1-hydroxy-bishomopregnacalciferol; 2-(3'-hydroxypropylidene)-19-nor-1α,25-dihydroxyvitamin $D_3$ (E-isomer); 17-20 dehydro-2-methylene-19-nor-(20S)-1α,25-dihydroxyvitamin $D_3$ (E- and Z-isomers); 26-homo-1α,25-dihydroxyvitamin $D_3$; 26,27-Dimethyl-α,25-dihydroxyvitamin $D_3$; Vitamin $D_3$; 25-hydroxyvitamin $D_3$.

The invention also provides a method of preventing glaucoma in a subject at risk of developing glaucoma, comprising administering to at least one eye of the at risk subject a therapeutically effective amount of a vitamin D compound of the following formula:

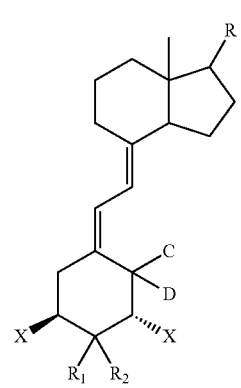

(Formula I)

wherein R is

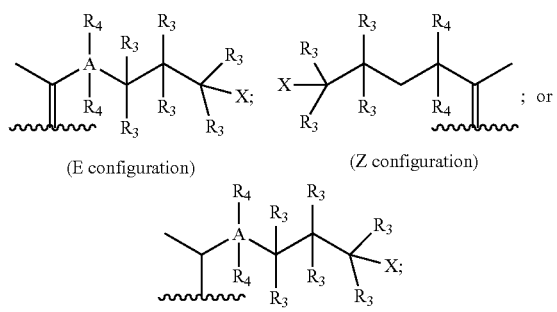

wherein $R_1$ and $R_2$ are H, methyl or 3'-hydroxypropylidine, or taken together as =$CH_2$ or methylene; wherein $R_3$ and $R_4$ are selected from H, alkyl (1-3 carbons), alkoxy, and can be the same or different from each other; wherein X is a hydroxyl or protected hydroxyl group; wherein A is oxygen or carbon, with the proviso that if A is oxygen, then $R_4$ is absent; and wherein C and D are H or taken together as =$CH_2$, wherein after administering the compound of formula I, the subject does not develop glaucoma.

By "glaucoma" we mean an eye disease that damages the optic nerve and impairs vision (sometimes progressing to blindness).

By "at risk for developing" glaucoma we mean any subject with a family history of ocular hypertension, or any subject exhibiting any risk factors of ocular hypertension, including poor eyesight, poor physical health, and the like.

Applicants note that the result of uniocular treatment is a bilateral IOP response. Therefore, treatment may be in both eyes or in either eye and result in successful treatment of OHT. For instance, OHT in a first eye may be reduced by treating either the first eye exhibiting the OTH, or in some cases, by treating only the second eye. In a preferred method, the eye exhibiting OHT is treated with the compounds of the present invention to reduce the OHT by at least 10%.

However, in a situation where a first eye is exhibiting OHT but direct treatment of that eye with the compounds of the present invention is not advisable (because, for instance, the eye is thoroughly bandaged and not receptive to eye drops), the OHT in the first eye may be reduced by treating the second eye (which may or may not be exhibiting OHT) with the compounds of the present inventions. The OHT in the first untreated eye typically experiences approximately 20% less reduction in OHT as compared to the treated eye.

One of skill in the art will understand how to accommodate treatment to compensate for this bilateral response.

Administration and Dose.

The composition of the present invention is intended to therapeutically treat conditions of the eye itself or the tissue surrounding the eye. The composition of the present invention may be incorporated in the topical delivery systems of this invention in therapeutically active amounts, usually in amounts ranging from about 0.2 µg-1 mg per day, preferably 5 µg, most preferably 10 µg (+/−10%) per day.

The composition may be applied to the patient daily. In one preferred embodiment, the composition may be applied to the patient one to two times daily, for each eye to be directly treated. The composition may be applied to the entire surface of the eye in a therapeutically effective amount, the exact amount depending on the factors such as age and general health condition of the patient to whom the composition of the present invention is being administered must be considered. Thus, a patient under age 10 will be treated with a concentration of the vitamin D compound of the present invention which may be less than that used for an older patient. These variations in concentration can be adjusted readily by the skilled practitioner. The details set out herein when coupled with a physician's skills will readily enable the physician to maximize the treatment regime for a particular patient.

The composition of the present invention can be administered to the eye by known means of administering other medicaments to the eye. For example, the composition, suitably formulated, can be administered in the form of eye drops or with ocular inserts. Suitable formulations may also incorporate standard eye vehicles which are physiologically acceptable to the eye. Such vehicles can be solutions or ointments, as desired. Further, the composition of the present invention can be formulated in unit dosage form with non-active opthalmologically-acceptable carriers well known in the art, or with other active medicaments where treatment of other conditions of the eye, for example, infection, allergy or inflammation, is prescribed.

The term "unit dosage form" as used herein refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans. Examples of suitable unit dosage forms in accord with this invention are tablets, capsules, ocular inserts, dropperfuls, segregated multiples of any of the foregoing, and other forms as are known in the art. The composition of the present invention may be easily prepared in unit dosage form with the employment of pharmaceutical materials which themselves are available in the art and can be prepared by established procedures.

The composition of the present invention may be applied to eyes without further formulation as eye drops. The composition of the present invention may also be formulated in solutions, ointments, creams, gels, sprays or any other form together with pharmaceutically acceptable carriers for topical application. The composition of the present invention may be also applied alone, in either diluted or concentrated form, without further formulation as a topical pharmaceutical agent. Solutions, i.e., dilute aqueous preparations containing the composition of the present invention and preservatives but without substantial concentrations of thickeners, can be sprayed upon the affected surface as by an aerosol pump. This type of delivery may be of value for treating larger areas, or for use with subjects having trouble administering eye drops.

The composition of the present invention may also be used in a pharmaceutical formulation containing antimicrobials, including antibiotics, antifungals, and other anti-viral compounds, which may complement or supplement the activity of the basic composition. Suitable antibiotics include tetracycline, polymyxin B or other common antibiotics used in topical compositions, especially over-the-counter formulations. Examples of useful antifungals include tolnaftate and micatin. Examples of anti-virals include interferon, either natural or recombinant, as well as nucleoside analogs, e.g., acyclovir. Counter-irritants such as camphor and menthol, drying agents such as benzyl alcohol, resorcinol and phenol, and astringents such as zinc sulfate and tannic acid can also be added to the composition as can other types of agents such as emollients, preservatives, antioxidants, color additives, lubricants or moisturizers.

The composition of the present invention may be prepared in almost any relatively inert topical carrier. Generally, the composition could take several forms, e.g., a polymer, a hydrogel, a cream, a gel, an ointment, a wax and/or a solution, capable of effectively retaining the physiologically active compounds of the present invention. Each of these formulations may contain the composition of the present invention as well as microorganism growth inhibitors (preservatives) and other additives above noted. Many such carriers are routinely used and can be obtained by reference to standard pharmaceutical texts. Examples include polyethylene glycols (PEG), polypropylene glycol copolymers, and some water soluble gels. A preferred carrier is an emulsified cream, but other common carriers such as certain petrolatum or mineral oil-based ointments in which the composition of the present invention is dispersible can be substituted.

Gels, i.e., thickened aqueous polymer or alcoholic solutions, containing the composition of the present invention and stabilizers may be clear and/or colored with suitable dyes. Suitable thickeners may include carboxymethylcellulose, polyvinylpyrrolidone or polyacrylic acid salts. Hydrogels may be used to provide a delayed-release of the physiologically active compounds of the present invention to the eye [Eremeev, 2006].

Ointments employed in practicing the present invention may be prepared utilizing known pharmaceutical techniques with conventional vehicles. For instance, hydrophilic or hydrophobic ointments may also be employed as carriers. However, hydrophobic ointments, such as petroleum jelly, which are based upon hydrocarbon and wax derivatives may not be as efficacious as the hydrophilic ointments because they may impede penetration into the skin. Hydrophilic ointments such as those based upon propylene glycol, polyalkylene glycols, and the propylene glycol copolymers are therefore preferred for ointment formulations. Propylene glycol, as a base, is preferable to polyethylene glycol. Wax formulations may also be employed in some situations where ease of application is a primary objective.

The composition of this invention can be formulated in any other suitable manner. For example, diclofenac sodium may be dissolved and added by sterile filtration to a preparation containing sodium chloride, hydroxypropyl methyl cellulose and surfactant. This mixture may then be adjusted to the appropriate pH by known techniques, for example by the addition of sodium hydroxide. Other methods will be apparent to one skilled in the art.

The composition of the present invention may also contain surfactants and, if desired, adjuvants, including additional medicaments, buffers, antioxidants, tonicity adjusters, preservatives, thickeners or viscosity modifiers, and the like. Additives in the formulation may desirably include sodium chloride, EDTA (disodium edetate), and/or BAK (benzalkonium chloride) or sorbic acid. Additional additives may include antioxidants, fragrance, color, water, preservatives (either antioxidants or antimicrobials), lubricants, moisturizers, or drying agents.

The composition may be formulated as an aqueous suspension. In general, aqueous suspensions suitable for topical ophthalmic administration may be formulated and administered in accordance with techniques familiar to persons skilled in the art. The finished suspensions are preferably stored in opaque or brown containers to protect them from light exposure, and under an inert atmosphere. These aqueous suspensions can be packaged in preservative-free, single-dose non-reclosable containers. This permits a single dose of the medicament to be delivered to the eye as a drop or ribbon, with the container then being discarded after use. Such containers eliminate the potential for preservative-related irritation and sensitization of the corneal epithelium, as has been observed to occur particularly from ophthalmic medicaments containing mercurial preservatives. Multiple dose containers can also be used, if desired, particularly since the relatively low viscosities of the aqueous suspensions of this invention permit constant, accurate dosages to be administered dropwise to the eye as many times each day as necessary.

Aqueous suspensions of the present invention may be formulated so that they retain the same or substantially the same viscosity in the eye that they had prior to administration to the eye. Alternatively, suspensions of the present invention may be formulated so that there is increased gelation upon contact with tear fluid. For instance, when a formulation containing DURASITE™ is administered to the eye at a lower pH, the DURASITE™ system swells upon contact with tears. This gelation or increase in gelation leads to entrapment of the suspended drug particles, thereby extending the residence time of the composition in the eye.

Aqueous solutions used in accordance with this invention may be formulated, for example, in accordance with the procedures set forth in Chapter 83 of Remington's Pharmaceutical Sciences, 14th Edition, Mack Publishing Company. Such ophthalmic solutions are sterile and may contain a bacteriological preservative to maintain sterility during use. The quaternary ammonium bacteriostats such as benzalkonium chloride are satisfactory for this purpose. An antioxidant may also be employed if desired. By way of example, suitable antioxidants include sodium bisulfite, N-acetylcysteine salts, sodium ascorbate and other water soluble ophthalmologically acceptable antioxidants known to the pharmaceutical art.

In one embodiment, the composition of the present invention incorporates insoluble polymers to provide a gel or liquid drops which release the drug over time. The composition may contain water soluble polymers or water insoluble polymers as the suspending agent. Examples of such soluble polymers are cellulosic polymers like hydroxypropyl methylcellulose. Water insoluble polymers are preferably crosslinked carboxy-vinyl polymers. The polymer may comprise about 0.1 to about 6.5%, more preferably about 1.0 to about 1.3% by weight based on the total weight of the suspension of a cross-linked carboxy-containing polymer. Suitable carboxy-containing polymers for use in the present invention and method for making them are described in U.S. Pat. No. 5,192,535 to Davis et al. which is hereby incorporated by reference and relied upon. These polymer carriers include lightly cross-linked carboxy-containing polymers (such as polycarbophil), dextran, cellulose derivatives, polyethylene glycol 400 and other polymeric demulcents such as polyvinylpyrolidone, polysaccharide gels and GELRITE™. A carboxy-containing polymer system such as DURASITE™, containing polycarbophil, a sustained release topical ophthalmic delivery system that releases the drug at a controlled rate, may also be used.

Aqueous mixtures of this invention may also contain amounts of suspended lightly cross-linked polymer particles ranging from about 0.1% to about 6.5% by weight, and preferably from about 0.5% to about 4.5% by weight, based on the total weight of the aqueous suspension. They will preferably be prepared using pure, sterile water, preferably deionized or distilled, having no physiologically or ophthalmologically harmful constituents, and will be adjusted to a pH of from about 4.0 to about 6.8, and preferably from about 5.5 to about 6.5, using any physiologically and ophthalmologically acceptable pH adjusting acids, bases or buffers, e.g., acids such as acetic, boric, citric, lactic, phosphoric, hydrochloric, or the like, bases such as sodium hydroxide, sodium phosphate, sodium borate, sodium citrate, sodium acetate, sodium lactate, THAM (trishydroxymethylaminomethane), or the like and salts and buffers such as citrate/dextrose, sodium bicarbonate, ammonium chloride and mixtures of the aforementioned acids and bases.

When formulating the aqueous suspensions, the osmotic pressure may be adjusted to from about 10 milliosmolar (mOsM) to about 400 mOsM, using appropriate amounts of physiologically and ophthalmologically acceptable salts. Sodium chloride is preferred to approximate physiologic fluid, and amounts of sodium chloride ranging from about 0.01% to about 1% by weight, and preferably from about 0.05% to about 0.45% by weight, based on the total weight of the aqueous suspension, will give osmolalities within the above-stated ranges. Equivalent amounts of one or more salts made up of cations such as potassium, ammonium and the like and anions such as chloride, citrate, ascorbate, borate, phosphate, bicarbonate, sulfate, thiosulfate, bisulfate, sodium bisulfate, ammonium sulfate, and the like can also be used in addition to or instead of sodium chloride to achieve osmolalities within the above-stated ranges. Sugars like mannitol, dextrose, glucose or other polyols may be added to adjust osmolarity.

The amounts of insoluble lightly cross-linked polymer particles, the pH, and the osmotic pressure chosen from within the above-stated ranges will be correlated with each other and with the degree of cross-linking to give aqueous suspensions having viscosities ranging from about 500 to about 100,000 centipoise, and preferably from about 5,000 to about 30,000 or about 5,000 to about 20,000 centipoise, as measured at room temperature (about 25° C.) using a Brookfield Digital LVT Viscometer equipped with a number 25 spindle and a 13R small sample adapter at 12 rpm. Formulations of the present invention should have a viscosity that is suited for the selected route of administration. Viscosity up to about 30,000=drop. About 30,000 to about 100,000 centipoise is an advantageous viscosity range for ophthalmic administration in ribbon form. When water soluble polymers are used, such as hydroxypropyl methylcellulose, the viscosity will typically be about 10 to about 400 centipoises, more typically about 10 to about 200 centipoises or about 10 to about 25 centipoises.

Kits.

In an alternate embodiment of the invention, a kit for conducting the methods of the present invention is provided. In one embodiment, the kit comprises a vitamin D compound according to the present invention and instructions for use.

In a preferred embodiment, the kit comprises a powdered form of at least one vitamin D compound according to the present invention, wherein the powdered vitamin D compound is hydrated by the user for immediate use, such as in a dual syringe device to form a precursor liquid that rapidly gels. Optionally, the kit may contain a solution for dissolving the vitamin D.

In an alternate embodiment, the kit comprises at least one vitamin D compound according to the present invention formulated, delivered and stored for use in physiologic conditions.

By "instructions for use" we mean a publication, a recording, a diagram, or any other medium of expression which is used to communicate the usefulness of the invention for one of the purposes set forth herein. The instructional material of the kit can, for example, be affixed to a container which contains the present invention or be shipped together with a container which contains the invention. Alternatively, the instructional material can be shipped separately from the container or provided on an electronically accessible form on a internet website with the intention that the instructional material and the biocompatible hydrogel be used cooperatively by the recipient.

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

III. EXAMPLES

The Examples described below show that the vitamin D compounds of the present invention can reduce intraocular pressure (TOP) and ocular hypertension (OHT) in subjects suffering therefrom. These examples provide the basis for the further development of vitamin D compounds for treating and preventing disorders such as glaucoma, Given that vitamin D is the endogenously synthesized "magic pill" or "sunshine" vitamin [Holick, 2008] able to prevent and to cure a number of diseases, its use for the treatment of ocular hypertension and glaucoma may provide other positive, beneficial side effects.

Example 1

Treatment of OHT with 1.25 $(OH)_2D_3$, AGR and 2MD

The Examples below disclose compounds and methods used to reduce OHT by reducing primate intraocular pressure (TOP).

Materials and Methods.

1,25-Dihydroxyvitamin $D_3$ (1,25$(OH)_2D_3$), AGR and 2MD compounds were >=98% pure.

Animals, Anesthesia.

Ocular normotensive adult cynomolgus monkeys (*Macaca fascicularis*), of either sex, weighing 3-7 kg were anesthetized with i.m. ketamine HCl (3-25 mg/kg, supplemented with 1-10 mg/kg) for IOP and topical drop administration. All monkeys were free of any ocular abnormalities according to slit lamp biomicroscopy at the time measurements were taken. The monkeys were provided by the Primate Center at the University of Wisconsin-Madison. All experiments were done in accordance with the ARVO Statement on the Use of Animals in Ophthalmic and Vision Research.

Treatments and IOP Measurements.

The intraocular pressure (IOP) was determined with a "minified" Goldmann applanation tonometer [Kaufman, 1980] using HALF AND HALF™ creamer solution (Borden) as the tear film indicator [Croft, 1997] with the monkey lying prone in a head holder and the eyes positioned 4 to 8 cm above the heart. All monkeys were examined by slit-lamp before the first IOP measurement in each protocol. For each eye, two or three IOP measurements were averaged as a baseline.

Under ketamine anesthesia (KETAJECT™, Phoenix Pharmaceutical, St Joseph, Mo. (3-25 mg/kg i.m., supplemented with 1-10 mg/kg i.m. as needed) baseline IOP was determined, usually between 7:30 and 9 am (2 readings, 5 minutes apart; if IOP baseline measurements were not within 2-3 mm Hg of each other, a $3^{rd}$ reading was taken 5 min later). Baseline IOP was at least 15 mmHg if possible. A baseline blood sample was taken from the femoral artery or vein, or sometimes the brachial vein (1-2 ml). This was allowed to clot and then spun down (3000 rpm for 10 min, Damon/IEC NH-SII centrifuge) and the serum removed and frozen at −20 C for no more than 1 week. Baseline systolic, diastolic and mean arterial pressure as well as heart rate were recorded with the Dinamap monitor from a cuff placed around the arm or the leg.

After baseline measurements, the monkey was place supine with the eye pointing up and the eyelid held open. A 5 µl drop of test material or vehicle was delivered to opposite eyes. The eyelid was held open for at least 30 sec and the eye was maintained in the upward position for an additional 30 sec. The monkey was then returned to its cage and allowed to wake up. In the afternoon, at least 6 hours after the morning treatment, another treatment was administered. On the second day, dosing was repeated in the am and pm.

On the $3^{th}$ day, prior to the $5^{th}$ treatment, baseline IOP, biomicroscopy and MAP were determined. Preliminary studies indicated an effect was observed after these treatments but not after a single treatment. Following the $5^{th}$ dose, IOP was measured at 1, 2, 3, 4, 5, 6, 7, 8, 12 (if possible), 24, and sometimes 48 hr. Biomicroscopy was done at 1, 3, 6, 24 and sometimes 48 hr. MAP on day 3 (some protocols) was determined at 1, 2, 3, 4, 5, 6, 7, 8, 24 and sometimes 48 hr if possible. Blood samples after the $5^{th}$ treatment were collected at 6, 24, and sometimes 48 hr. For some protocols, IOP was also measured prior to each treatment; MAP was measured prior to the morning treatment; blood was collected prior to the afternoon treatment. Subsequent screening protocols will not include the MAP and blood collections and will only measure IOP at baseline and prior to and for 1-6 hr after the $5^{th}$ treatment.

Data Analysis.

Empirically, we found that approximately 8-10 experiments are required for any drug dose in order to obtain a reliable quantitative, statistically testable estimate of the response. Formal sample size calculations have corroborated this impression, as hereafter described. Generally speaking, we wished to identify mean physiologic responses that were >25% of the baseline value (adjusted for non-drug or non-stimulus-related baseline drift) and >1.5 SD of the mean response. The following standard equation for sample size calculation was used: $N=2 (Z\alpha+Z\beta)_2/\delta/\sigma)_2$, where $Z\alpha=1.645$ or $1.960$ for one-sided and two-sided 5% significance, respectively; $Z\beta=0.84$ or $1.282$ for 80% and 90% power, respectively; $\delta$ $\delta$=population standard deviation; $\sigma$=the difference (i.e., response) in the parameter being measured ($\delta$ and $\sigma$ must have the same units). From that equation, it was determined that 5.5 experiments were required to detect differences of 1.5 standard deviations in a paired test at a one-sided 5% significance level with 80% power, while 9.3 experiments were needed to detect such a difference at a two-sided 5% significance level with 90% power.

Data are expressed as the mean±s.e.m. Significance was determined by the two-tailed paired t-test for ratios compared to 1.0 or differences compared to 0.0.

Results

Vitamin D Compounds as Ocular Hypotensive Agents (FIG. 1).

The effects of propylene glycol vehicle alone on IOP were compared to diurnal IOP in the untreated opposite eye. Prior to the first treatment, baseline IOP in treated and control eyes was 18.8±1.2 and 19.3±1.3 mmHg, respectively (n=8). Prior to the $5^{th}$ treatment, there was no difference in IOP in either eye compared to baseline. After the $5^{th}$ treatment, IOP gradually decreased by 4-15% over the next 8 hr in both eyes. IOP in the treated eye was consistently, but not significantly, less than in the control eye at nearly all time points. The diurnal decline in IOP has been previously reported [Gabelt, 1994]. There was no ocular inflammation at any time-point.

Figure 2A:
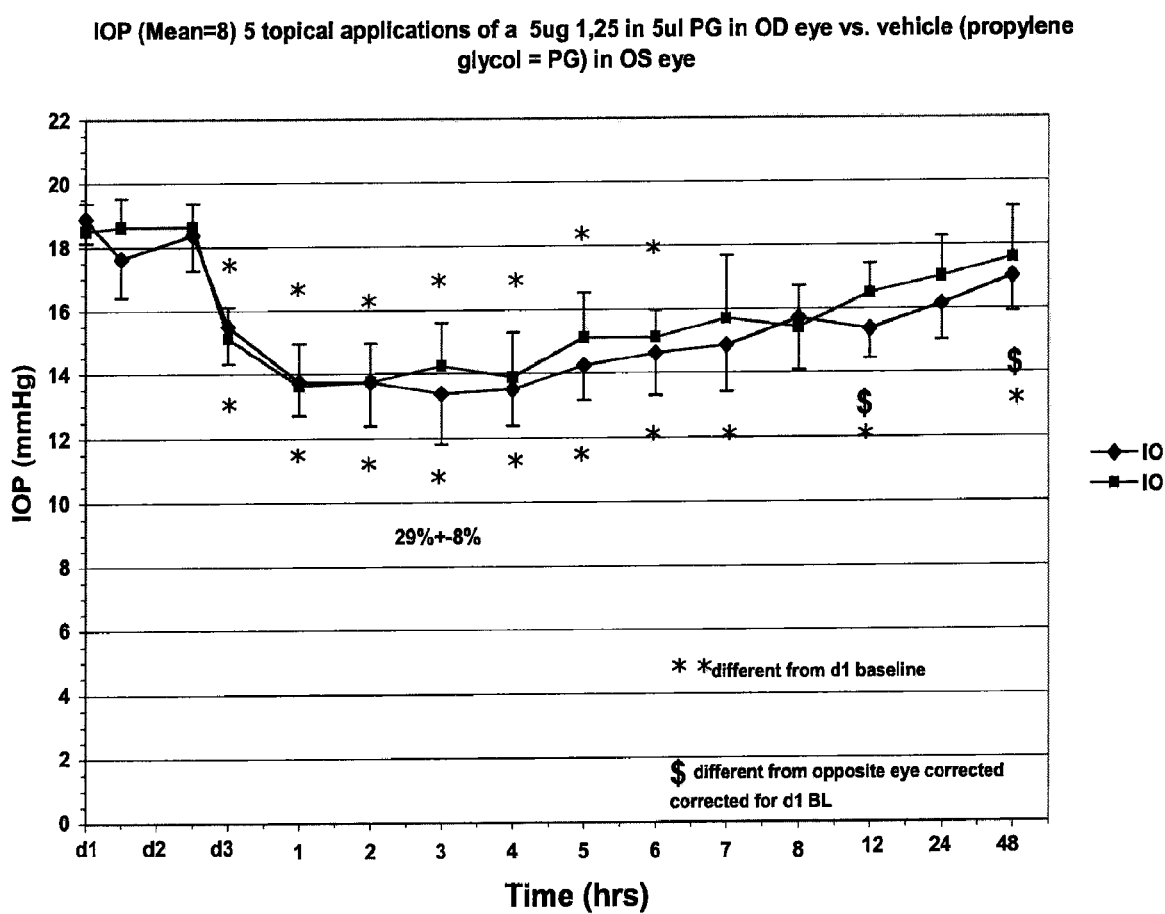
FIG. 2 depicts an IOP response after the 5th dose of twice daily treatments with 5 μg 1,25-Dihydroxyvitamin $D_3$ in 5 μl propylene glycol in one eye and vehicle (5 μl propylene glycol in opposite eye). (A) (mean=8); (B) (mean=5).
Figure 2B:
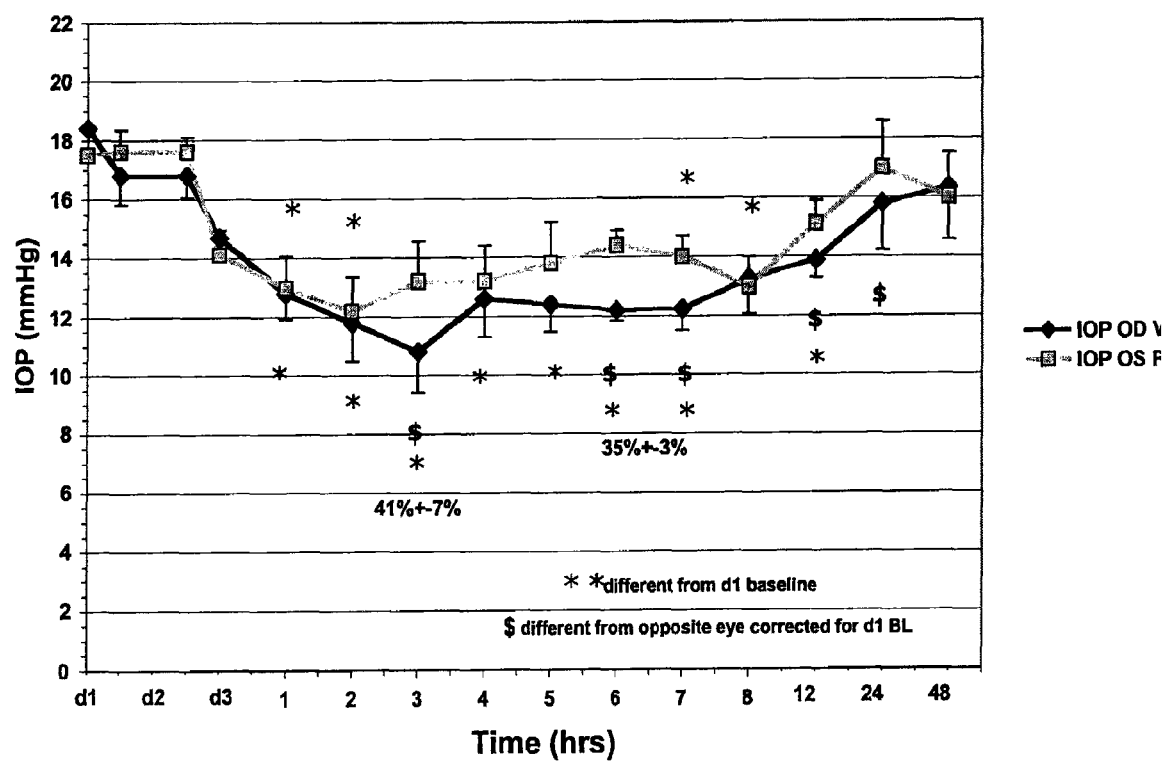
Figure 3:
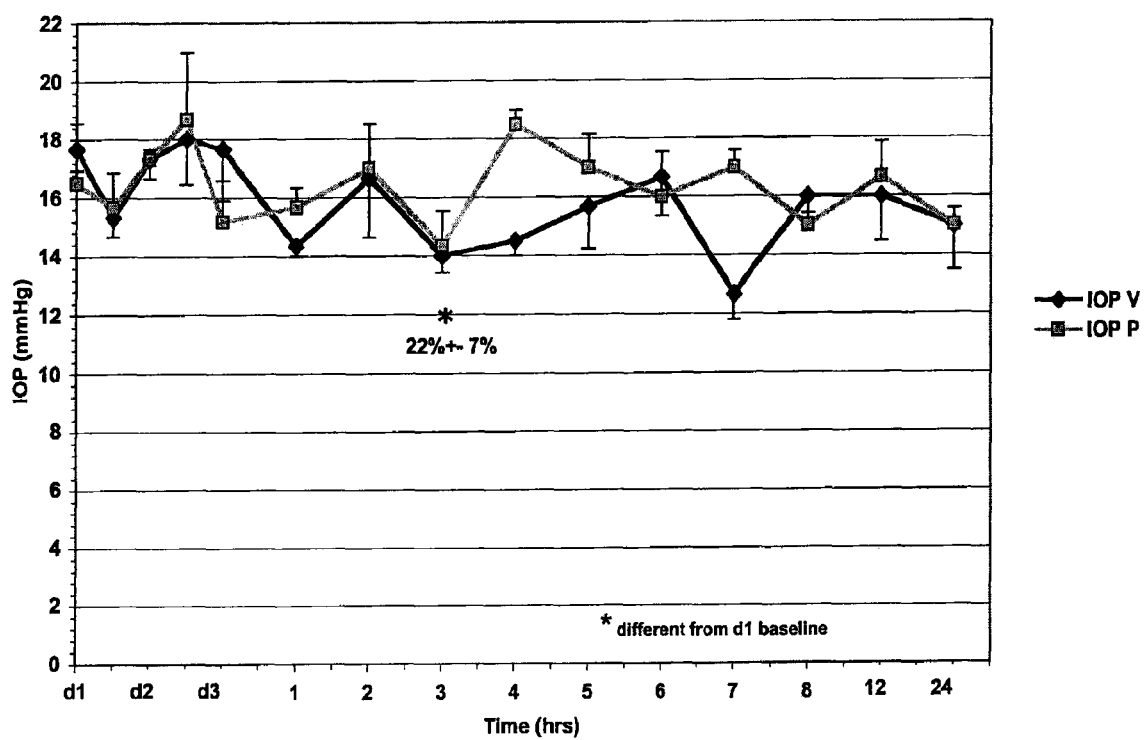
FIG. 3 depicts an IOP response after the 5th dose of twice daily treatments with 5 μg AGR in 5 μl propylene glycol in one eye and vehicle (5 μl propylene glycol) in the opposite eye.
Figure 4:
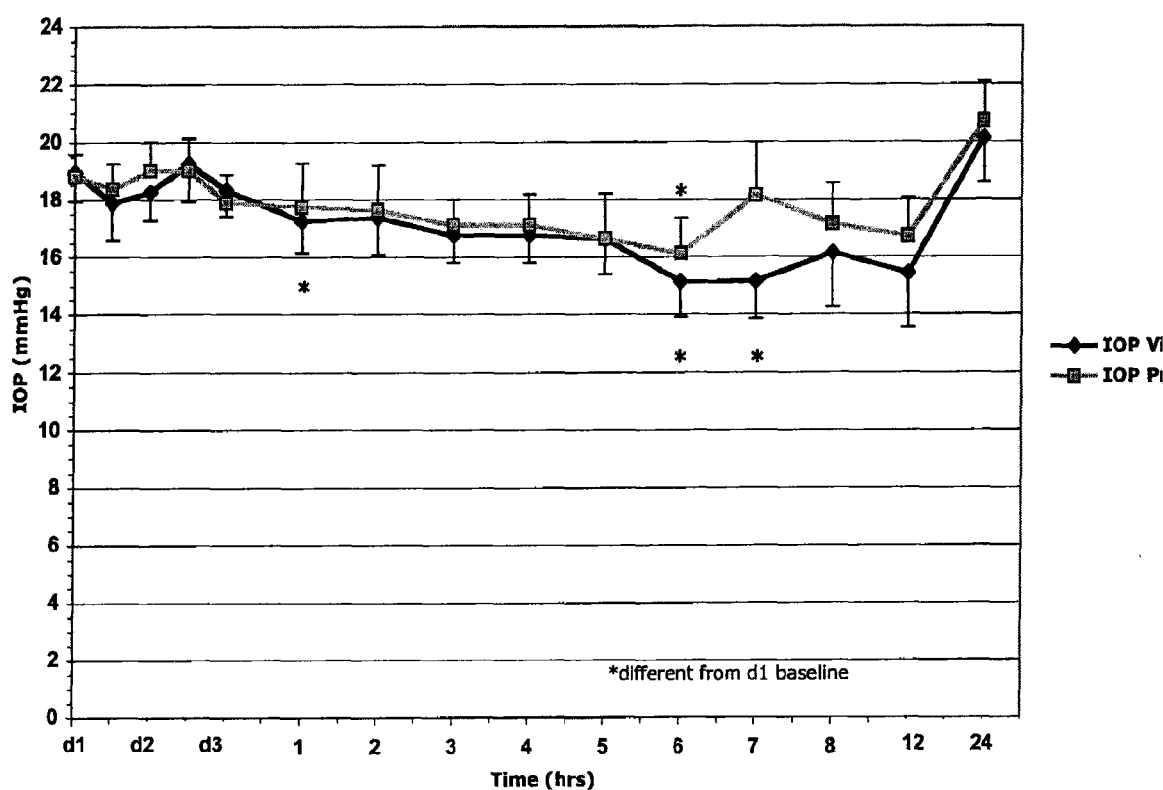
FIG. 4 depicts an IOP response after the 5th dose of twice daily treatments with 6 μg 2MD in 5 μl propylene glycol in one eye and vehicle (5 μl propylene glycol) in the opposite eye.
Figure 5:
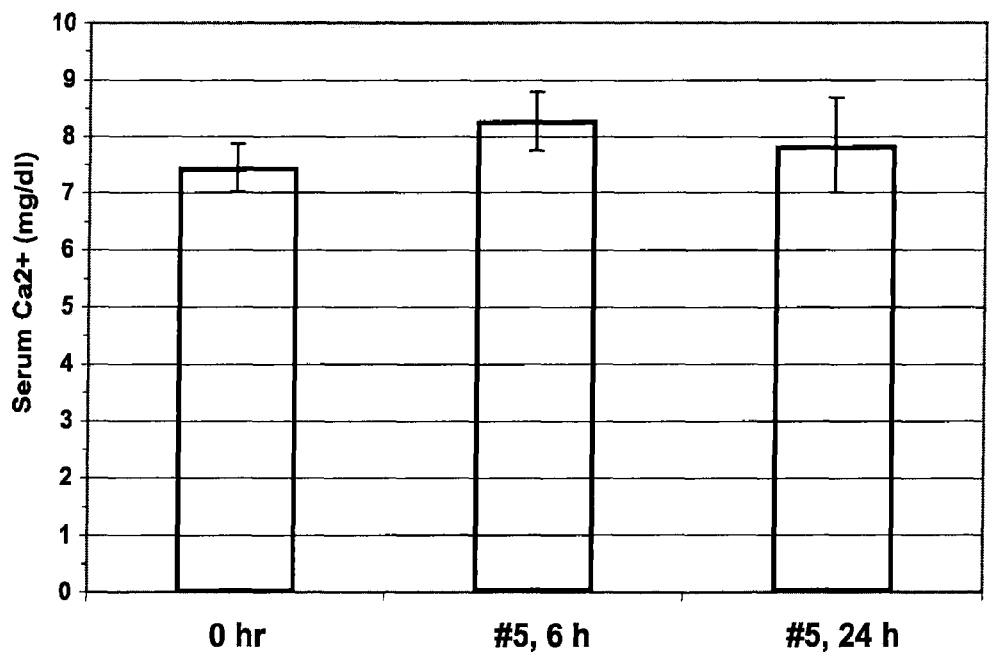
FIG. 5 depicts a mean serum $Ca^{2+}$ Level (n=4) in monkeys during 5 topical applications of 5 μl propylene glycol in one eye vs. the untreated opposite eye.
Figure 6:
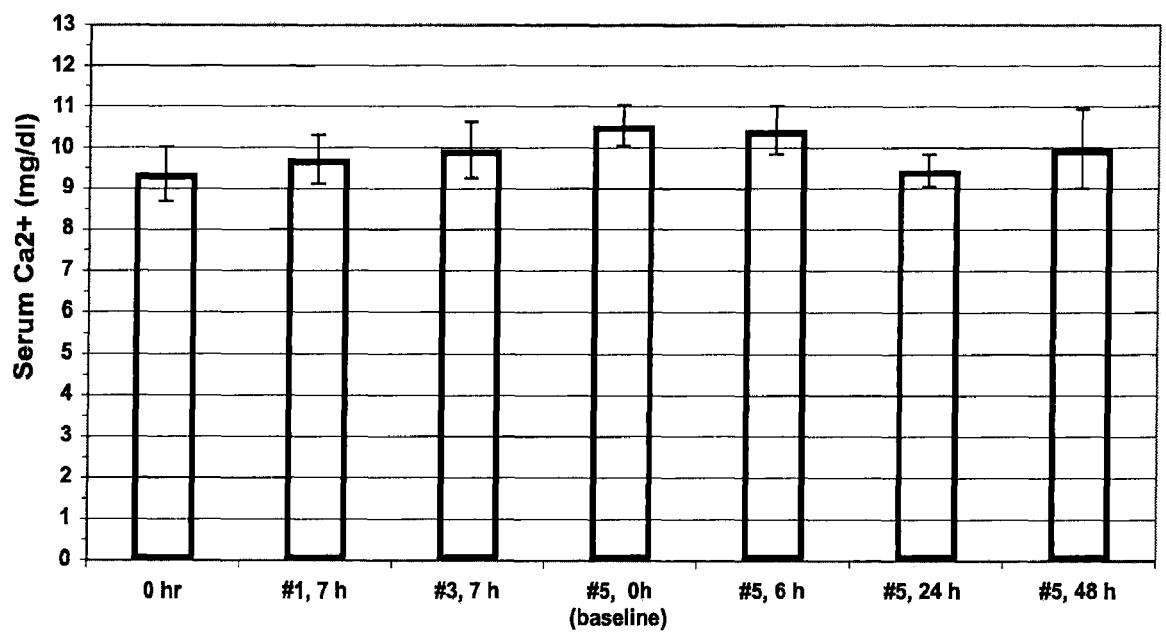
FIG. 6 depicts a mean serum $Ca^{2+}$ Level (n=8) in monkeys during topical applications #1-5 of 5 μg 1,25-Dihydroxyvitamin D3 in 5 μl propylene glycol in one eye vs. 5 μl propylene glycol in the opposite eye.
Figure 7:
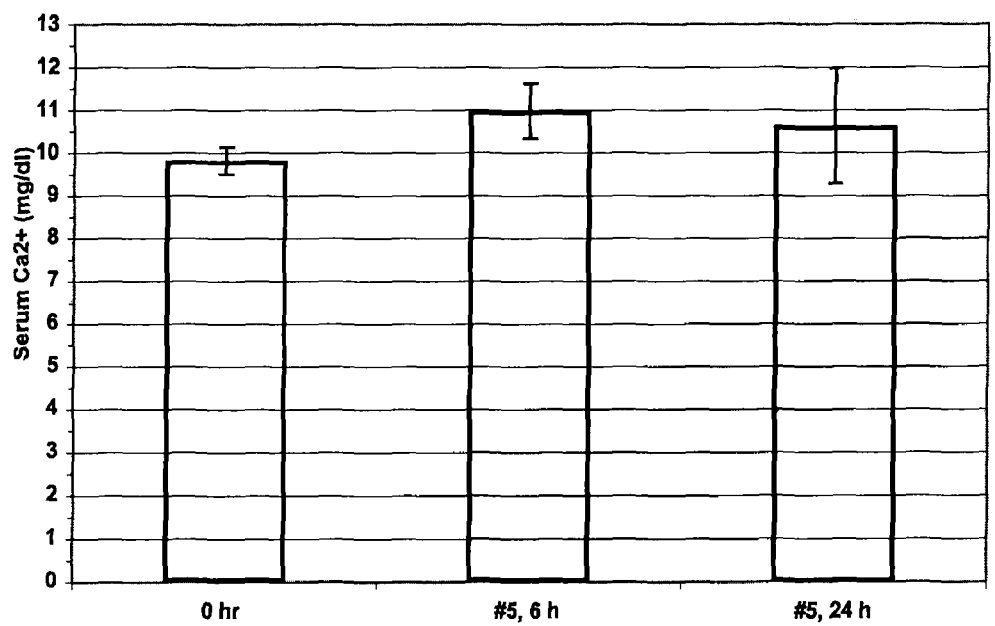
FIG. 7 depicts a mean serum $Ca^{2+}$ Level (n=4) in monkeys after the $5^{th}$ topical application of 5 μg AGR in 5 μl propylene glycol in one eye vs. 5 μl propylene glycol in the opposite eye.
Figure 8:
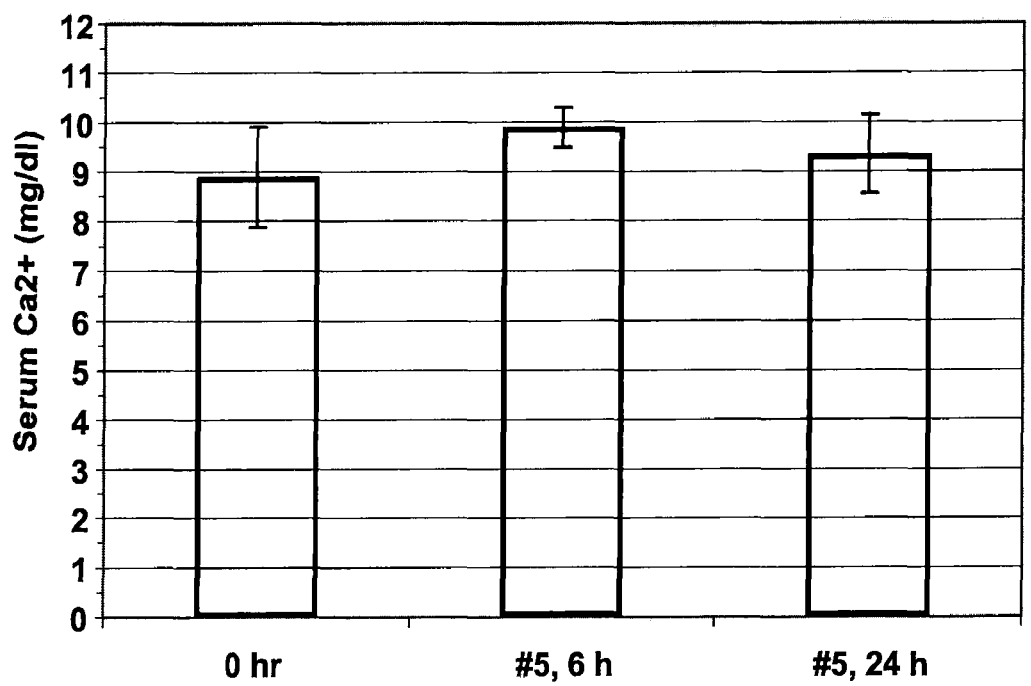
FIG. 8 depicts a mean serum $Ca^{2+}$ Level (n=8) in monkeys after the $5^{th}$ topical application of 6 μg 2MD in 5 μl propylene glycol in one eye vs. 5 μl propylene glycol in the opposite eye.

1,25-Dihydroxyvitamin $D_3$ (FIGS. 2A and 2B).

Prior to the first treatment, baseline IOP in treated and control eyes was 18.9±0.7 and 18.5±0.9 mmHg, respectively (n=8). Prior to the $5^{th}$ treatment, IOP in both treated and control eye was approximately 3-4 mmHg (~17%, p<0.05, n=8)) less than at baseline. After the $5^{th}$ treatment, IOP continued to decrease by an additional 1-2 mmHg (total reduction of ~20-30%, p<0.02) from hr 1-4 followed by a gradual recovery toward baseline by 24-48 hr. IOP in the treated eye was consistently, but not significantly less than in the control eye at nearly all time points. There was no ocular inflammation at any time-point.

AGR (FIG. 3).

Prior to the first treatment, baseline IOP in treated and control eyes was 16.5±1.3 and 15.9±1.6 mmHg, respectively (n=4). Prior to the $5^{th}$ treatment, IOP in both treated and control eye was no different than at baseline. After the $5^{th}$ treatment, IOP was not significantly decreased in the treated eye except at the 3 hr time point. There was no change in IOP in the control eye and no difference between the eyes at any time-point. There was no ocular inflammation at any time-point.

2MD (FIG. 4).

Prior to the first treatment, baseline IOP in treated and control eyes was 18.9±1.0 and 18.8±0.8 mmHg, respectively (n=8). Prior to the $5^{th}$ treatment, IOP in both treated and control eye was no different than at baseline. After the $5^{th}$ treatment, IOP gradually decreased over the next 8 hours similar to the diurnal decline seen with vehicle alone. There may have been a small drug effect at 6 and 7 hours. There was no ocular inflammation at any time-point.

Serum $Ca^{2+}$ Level after the Ocular Topical Applications of Vitamin D Compounds.

There were no significant serum $Ca^{2+}$ level increase past treatments (FIG. 5-8), indicating that vitamin $D_3$ compounds probably do not enter into systemic circulation.

Discussion.

Propylene glycol (vehicle) did not change the IOP in monkeys. Vitamin $D_3$ compounds applied at the same dose: 5 uniocular topical treatments (2 topical treatments at 10 μg per day) exhibited ocular hypotensive effect depending on the compound's structure (1,25(OH)$_2$D$_3$>2MD>AGR). The strongest response (up to 40% IOP decrease) was observed for 1,25(OH)$_2$D$_3$. The IOP decrease was bilateral or the treatment of one eye caused the IOP decrease in the opposite contralateral eye by unknown mechanism.

The bilateral IOP lowering response following unilateral topical administration 1,25(OH)$_2$D$_3$ may be due to systemic absorption or transfer to the contralateral eye by the monkey rubbing its eyes. Transfer via systemic absorption is possible since the dose of 1,25(OH)$_2$D$_3$ was very high even though the volume administered was small (5 μl). It is also possible the monkey could have transferred material to the opposite eye by rubbing although that would not explain the effect after the $5^{th}$ dose since the monkey was anesthetized the entire time following this dose while the IOP experiment was conducted. The fact that serum $Ca^{2+}$ level is not significantly increased after 5 doses of any compound's administration (FIG. 6-8) argues against vitamin $D_3$ compounds' entering into the system. Since the vitamin $D_3$ compounds are highly lipid soluble, they could potentially penetrate the blood-brain barrier and mediate IOP effects via a yet unidentified central mechanism as has been proposed for some other compounds through CNS [Gabelt, 1994]. Another possibility is an afferent-to-efferent mechanism within the eye. Testing with lower doses of 1,25(OH)$_2$D$_3$ may help elucidate some of these possibilities.

The contralateral effect of topically administered β-blockers on intraocular pressure was further confirmed in the Ocular Hypertension Treatment Study (OHTS) with 1,636 human subjects. The most widely accepted theory regarding the mechanism of the contralateral effect of topically applied β-blockers is that systemic absorption of the β-blocker, primarily through the nasolacrimal mucosa, results in transport of the β-blocker to the contralateral eye through the bloodstream. Alternatively, systemic absorption may also result in centrally mediated effects on intraocular pressure control in the contralateral eye. The factor most strongly correlated with the magnitude of the contralateral effect was the magnitude of the IOP reduction in the treated eye. The greater the therapeutic effect, the greater the IOP reduction in the contralateral eye. Thus, the therapeutic effect may be underestimated if the contralateral eye is used as a "control".

The second most influential factor was the baseline IOP of the contralateral eye. The higher the baseline IOP of the contralateral eye, the greater the IOP reduction in the contralateral eye and this again would result in an underestimate of the therapeutic effect if the contralateral eye was used as a "control" [Piltz, 2000]. Contamination of the untreated eye by medication instilled into the tested eye has also been suggested. Another less widely held hypothesis is the consensual ophthalmotonic reaction in which alterations in the intraocular pressure of one eye result in a reflex intraocular pressure change in the fellow eye [Piltz, 2000].

In same cases, the contralateral IOP response is mediated, in part, through an effect in central nervous system. As was shown for topical administration of radiolabeled 8-hydroxy-2-dipropylaminotetralin, the redistribution of the drug through the systemic circulation to the contralateral eyes was minimal, which argues against redistribution of drug as being the reason for the contralateral ocular hypotensive response [Chidlow, 1999]. The topical, unilateral application of 7-hydroxy-2-dipropylaminotetralin (7-OH-DPAT) (75 mg), a dopamine $D_3$-preferring receptor agonist, decreased the intraocular pressure (TOP) bilaterally in a dose-dependent manner. The primary site of $D_3$ receptor-mediated action of 7-OH-DPAT is located on postganglionic sympathetic nerve endings in the ciliary body of rabbit. Suppression of activity of the peripheral sympathetic nervous system plays a role in the suppression of aqueous humor flow by 7-OH-DPAT [Chu, 2000].

Contralateral response was also observed after Selective Laser Trabeculoplasty procedure in treatment of glaucoma patients.

Example 2

Measuring IOP Reduction Following Treatment with Vitamin D Compounds

Monkeys Treatments and Intraocular Pressure (TOP) Measurements.

Adult cynomolgus monkeys (*Macaca fascicularis*) of either sex were anesthetized with intramuscular ketamine HCl (10 mg/kg initial, 5 mg/kg supplemental). Baseline pretreatment IOP was determined by Goldmann applanation tonometry [Kaufman, 1980] with cream used as a tear film indicator [Croft, 1997]. Two baseline IOP measurements were taken 5 minutes apart. Monkeys were then treated topically with 5 µl of 1,25-dihydroxyvitamin $D_3$ (1,25-$(OH_2)D_3$(0.1-5 µg) in propylene glycol to one eye and vehicle (propylene glycol) to the opposite eye twice a day for 5 treatments total. Drops were administered to the central cornea, one min apart, while the monkeys were in a supine position with their eyelids held open for at least 30 sec post drops. IOP was also measured prior to the afternoon treatment. On the third day, IOP was measured prior to the morning treatment. Following the fifth treatment, IOP was measured hourly for 8 hours and also at 12, 24 and 48 hours. Slit lamp examination (to determine the presence of biomicroscopic cells or flare) was performed prior to the $1^{st}$ IOP measurement and at hours 3 and 6 (24 and 48 hr where appropriate). Biomicroscopy was performed prior to the first and fifth treatment and at 3 and 6 hours after the fifth treatment. Monkeys were allowed to rest for at least 2 weeks between studies. There were 8 monkeys for each treatment group.

Figure 9A:
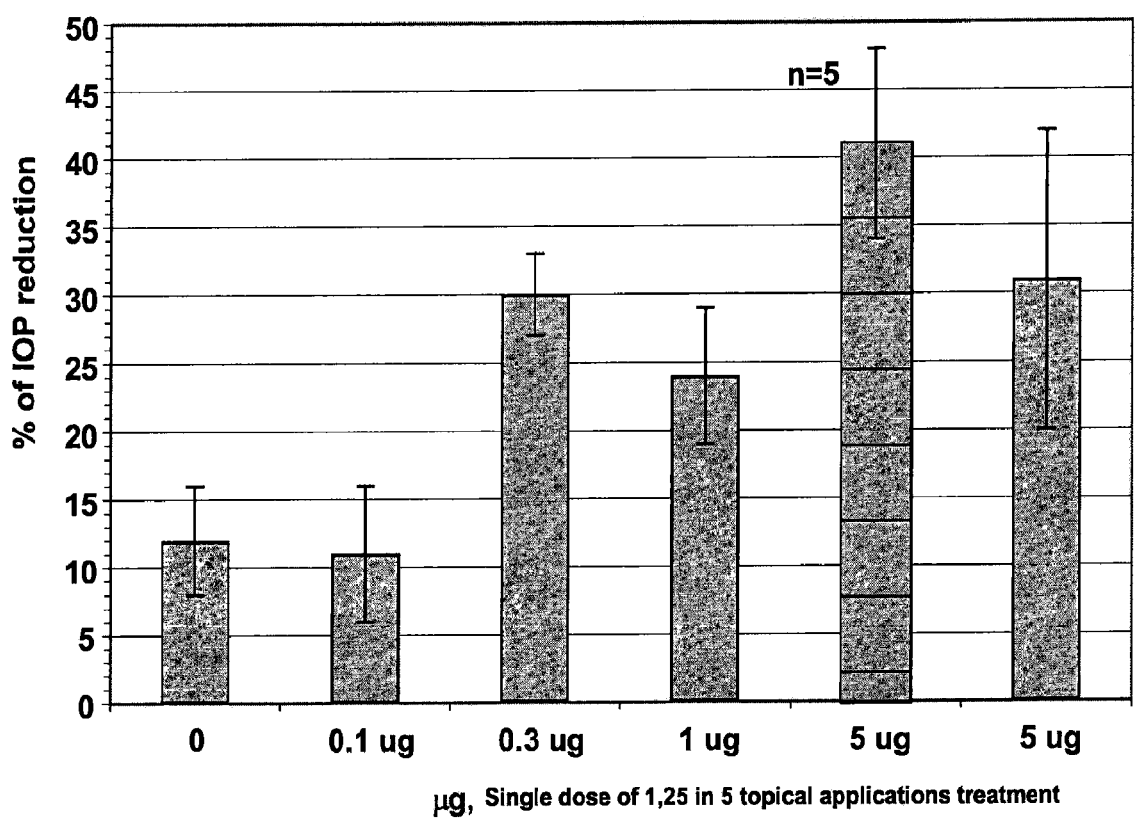
FIG. 9A depicts the dose dependence of the IOP decrease after 5 topical unilateral applications of 1α,25-dihydroxyvitamin $D_3$ in monkey eye.
Figure 9B:
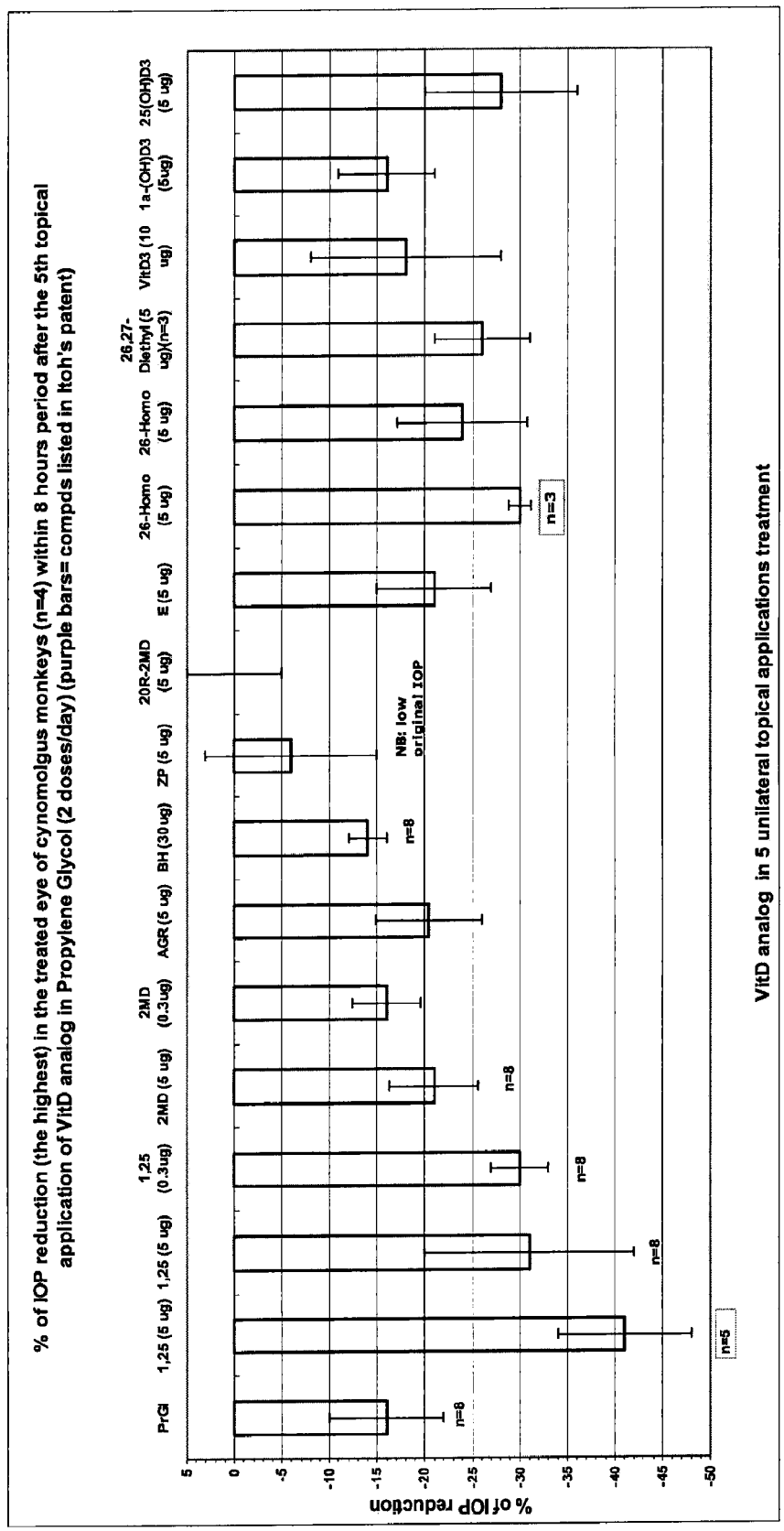
FIG. 9B is a bar graph depicting the percentage of IOP reduction after application of different vitamin D compounds.
Figure 9C:
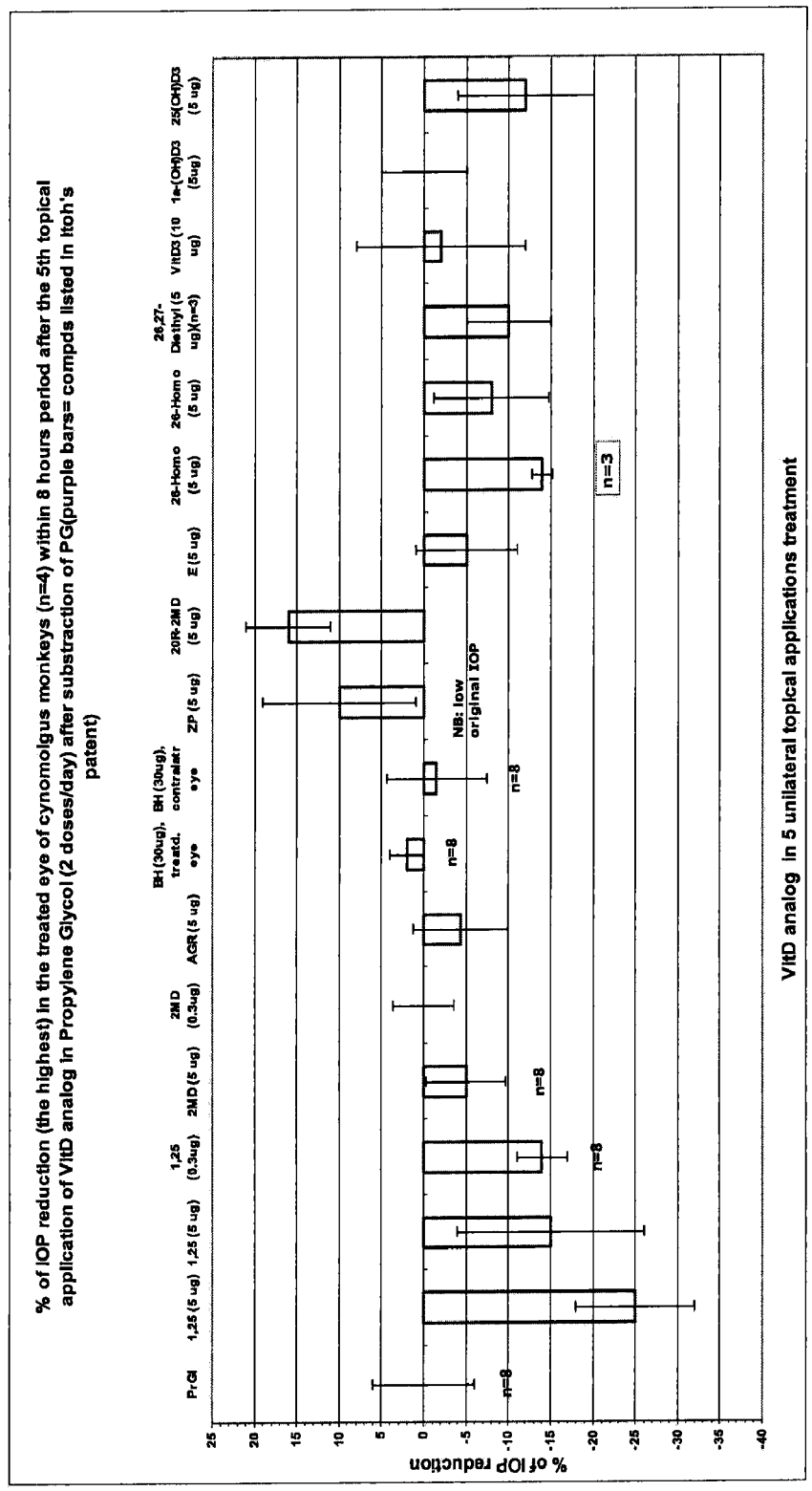
FIG. 9C is a bar graph indicating the percentage of IOP reduction after application of different vitamin D compounds after subtracting the propylene glycol (PG) effect (10%). If a deltaIOP is negative, the treatment has decreased IOP which is the desired effect.

FIGS. 9B and 9C show a summary of maximal ocular hypotensive effects (as a percentage of IOP reduction) of different vitamin D compounds as the result of 5 topical unilateral applications in monkey eye. Most compounds were tested in a group of 4 monkeys. If number of monkeys in the group was different, it is indicated in the box located next to the bar. Some compounds (at the same dose) are represented by two bars: one with all monkeys used in the group and the second bar is represented after exclusion of monkeys that had original low IOP or that had something wrong with them during the experiment (again the number in that group is shown in the box next to bar).

Example 3

Reducing the Intraocular Pressure without Changing the Aqueous Humor Dynamics

Materials and Methods.

All animal experiments were conducted in accordance with the University of Wisconsin IACUC and National Institutes of Health guidelines, and with the ARVO statement for the Use of Animals in Ophthalmic and Vision Research.

Animals and Diets.

Male Sprague-Dawley weanling rats were obtained from Harlan (Indianapolis, Ind.) and maintained on a highly purified vitamin D-deficient diet, containing 0.47% calcium and 0.3% phosphorus (Pi) supplemented 3 times a week with 500 µg DL-α-tocopherol, 60 µg menadione, and 40 µg β-carotene in 0.1 ml soybean oil (AEK) [Suda, 1970]. Rats were housed in hanging wire cages and maintained on a 12 h light/dark cycle. Rats fed the vitamin D-deficient diet were maintained in a room with incandescent lighting, and all potential sources of ultraviolet light and vitamin D were excluded. At 14 wk of age, blood was taken from the tail for measurement of serum calcium concentration. Severe hypocalcemia was used to confirm vitamin D depletion.

Animals and Anesthesia.

Ocular normotensive adult cynomolgus monkeys, of either sex, weighing 3-7 kg were anesthetized with i.m. ketamine HCl (3-25 mg/kg, supplemented with 1-10 mg/kg) for IOP, topical drop administration and aqueous humor flow measurements. All monkeys were free of any ocular abnormalities according to slit lamp biomicroscopy at the time measurements were taken. For outflow facility measurements, animals were given intravenous sodium pentobarbital (15 mg/kg, supplemented with 5-10 mg/kg) following i.m. ketamine induction.

Serum Calcium Analysis.

Blood samples from rats were obtained from the tail artery. Blood samples from monkeys were obtained from femoral arteries. Whole blood was centrifuged at 1100×g for 15 min at 25° C. to yield serum. Serum calcium concentration was determined on serum, diluted 1:40 with 1 g/L $LaCl_3$ (Halloran and DeLuca, 1981) using a 3110 atomic absorption spectrometer (Perkin Elmer, Norwalk, Conn.).

Experimental Design for Rat Microarrays Study.

Vitamin D-deficient rats were given one bolus intravenous dose of 730 ng of 1,25-$(OH)_2D_3$/kg of body weight in ethanol or ethanol vehicle (control). Rats were anesthetized with isofluorane and decapitated 1, 3, 6, 10 and 24 h after injection of the dose or vehicle. There were three rats in each group for each time point. Blood was collected at the same time for determination of changes in serum calcium concentration. For each rat, the first 15 cm of intestine (duodenum) was removed, slit longitudinally and scraped with a glass slide. The mucosa was placed in a vial with GTC extraction buffer supplemented with 2% of β-mercaptoethanol (PolyATtract System 1000, Promega Corp., Madison, Wis.), homogenized at high speed with PowerGen 700 (Fisher Scientific, Pittsburgh, Pa.), flash frozen in liquid $N_2$ and stored at −80° C. Experiments were done in duplicate.

Rat mRNA Preparation.

For each time point, Poly(A+) RNA was isolated from pooled homogenized mucosa of three 1,25-$(OH)_2D_3$ or three vehicle treated rats. The mRNA was isolated using the PolyATtract System 1000 (Promega Corp., Madison, Wis.). The mRNA was purified using an RNeasy kit (Qiagen, Chatsworth, Calif.). The quality, integrity and quantity of the Poly(A+) RNA were determined by agarose gel electrophoresis, UV absorption spectrophotometry and the use of Agilent Bioanalyser 2100 (Agilent Technologies, Palo Alto, Calif.).

Experimental Design and RNA Preparation for Mouse Microarrays Study.

Primary fetal mouse calvarial cells were isolated and cultured in αMEM containing 10% FBS as described

[Shevde, 2002]. Cells were plated in the 2×6-well plates ($5 \times 10^5$ cells/well) and cultured with medium changes performed on days 1 and 4. On day 4 cells on 1 plate were treated with 1,25(OH)$_2$D$_3$ (10 nM final concentration). Second plate was used as the control. After 24 h of incubation with 1,25(OH)$_2$D$_3$, cells were harvested and total RNA was isolated with Trizol reagent (Invitrogen Life Technologies, Carlsbad, Calif.). The mRNA was further purified using an RNeasy kit (Qiagen, Chatsworth, Calif.). The quality, integrity and quantity of the total RNA were assessed by agarose gel electrophoresis and UV absorption spectrophotometry. Experiments were done in triplicates.

Microarray Probe Preparation.

Double-stranded cDNA was synthesized from 3 μg of rat polyadenylated poly(A+) RNA or 13 μg mouse total RNA using the Superscript Choice system (Invitrogen Life Technologies, Carlsbad, Calif.), all according to the Affymetrix Gene Expression manual (Affymetrix, Inc., Santa Clara, Calif.). Following phenol/chloroform extraction and ethanol precipitation, a biotin-labeled in vitro transcription reaction was performed using the cDNA template and BioArray High Yield In Vitro Transcription kit (Enzo Life Sciences, Farmingdale, N.Y.). The cRNA was fragmented at 0.7-1.1 μg/μl final concentration in 1× fragmentation buffer (40 mM Tris-acetate, pH 8.1, 100 mM potassium acetate, 30 mM magnesium acetate). The size of cRNA before (0.5 kb and longer) and after (35-200 base fragments) fragmentation was checked by agarose gel electrophoresis.

Microarray Hybridization Procedure.

The hybridization reaction and the automated hybridization procedure were performed by the Gene Expression Center at the Biotechnology Center at the University of Wisconsin-Madison as described (Kutuzova, 2004). Each probe was tested on an Affymetrix Test3 Array and the quality of the cDNA and cRNA was determined by a 3'/5' ratio of housekeeping genes within the array (ubiquitin, rat glyceraldehyde 3-phosphate dehydrogenase, β-actin, and hexokinase). If the sample passed the quality control on the Affymetrix Test3 Array, it was hybridized to Affymetrix high-density rat oligonucleotide arrays (Rat Expression Array 230 2.0) or to mouse arrays (Mouse Genome 430 2.0 Arrays). (Affymetrix GeneChip® Expression Analysis Technical Manual; http://www.affymetrix.com/support/technical/manual/expressionmanual.affx). Expression data were analyzed using the Affymetrix Microarrray Suite software version 5.0 (MAS 5.0). Comparison tables for each time point for 1,25-(OH)$_2$D$_3$ vs. vehicle-treated rats were generated in EXCEL (Microsoft). For each comparison, e.g. 1,25-(OH)$_2$D$_3$ treated relative to control (vehicle treated), and for each cDNA represented in the array, a ratio (e.g. 1,25-(OH)$_2$D$_3$/control) and an absolute difference of intensities for 1,25-(OH)$_2$D$_3$ and vehicle treated were calculated. Microarray data validation was done by Quantitative Real Time PCR (Q-PCR) as described previously (Kutuzova, 2004).

Monkeys Treatments and Intraocular Pressure (IOP) Measurements.

Baseline pretreatment IOP was determined by Goldmann applanation tonometry [Kaufman, 1980] with cream used as a tear film indicator [Croft, 1997]. Two baseline IOP measurements were taken 5 minutes apart. Monkeys were then treated topically with 5 μl of 1,25-dihydroxyvitamin D$_3$ (1,25-(OH)$_2$D$_3$) (0.1-5 μg) to one eye and vehicle (propylene glycol) to the opposite eye twice a day for 5 treatments total. Drops were administered to the central cornea, one min apart, while the monkeys were in a supine position with their eyelids held open for at least 30 sec post drops. IOP was also measured prior to the afternoon treatment. On the third day, IOP was measured prior to the morning treatment. Following the fifth treatment, IOP was measured hourly for 8 hours and, in some cases, also at 12, 24, and 48 hours. Slit lamp examination (to determine the presence of biomicroscopic cells or flare) was performed prior to the 1$^{st}$ IOP measurement and at hours 3 and 6 (24 and 48 hr where appropriate). Monkeys were allowed to rest for at least 2 weeks between studies. There were 8 monkeys for each treatment group.

Aqueous Humor Formation Study.

Aqueous humor formation rate was determined by ocular scanning fluorophotometry (Fluorotron Master, OcuMetrics Inc, Mountain View, Calif.) as previously described [Rasmussen, 2007]. Fluorescein drops were administered at least 30 minutes after the fourth treatment (see above) with vitamin D or vehicle. On day 3, prior to the fifth treatment, IOP and biomicroscopy were done. Following the fifth treatment scans were taken hourly, beginning 1 hour after treatment, until 6 duplicates scans were collected. Baseline scans were collected for 6 hours within 2 weeks before and at least 2 weeks after the treatment study. Post treatment aqueous humor formation rates were compared to the average of the pre and post baseline scans and to the vehicle treated eyes by the paired t-test for ratios different from 1.0. There were 8 monkeys for each treatment group.

Outflow Facility Study.

Outflow facility was determined in pentobarbital-anesthetized monkeys [Gabelt, 2004] by two-level constant pressure perfusion of the anterior chamber with Bárány's perfusand [Bárány, 1964] (n=8). Four monkeys (group A) received the single bolus injection of 1 μl of 1 μg vitamin D 1,25-dihydroxyvitamin D$_3$ (1,25-(OH)$_2$D$_3$) into the anterior chamber of one eye (Treated eye) or 1 μl of propylene glycol into the anterior chamber of fellow eye (Control eye). Four monkeys (group B) were treated topically with 5 μg of vitamin D in 5 μl of propylene glycol or vehicle (5 μl of propylene glycol) twice daily for two days.

Following baseline outflow facility measurements on the third day, the fifth treatment was administered as a single bolus injection of 1 μl of 1 μg vitamin D 1,25-dihydroxyvitamin D$_3$ (1,25-(OH)$_2$D$_3$) into the anterior chamber of one eye (Treated eye) or 1 μl of propylene glycol into the anterior chamber of fellow eye (Control eye). Following injections, the treatment bolus was allowed to wash in for 5 min with flow from the reservoirs. Then the contents of the anterior chamber were mixed by blowing cold air on the cornea to create convection. Reservoirs were closed for 75 minutes, then reopened and outflow facility measured for 60-90 minutes. Data were averaged for the entire 60-90 minute period and for 30-minute intervals and then were compared to baseline and to the vehicle treated eyes. Ratios were compared by the two-tailed paired t-test for ratios different from 1.0.

Results

Vitamin D Modulates the Expression of Genes Involved in Regulating IOP.

Figure 10A:
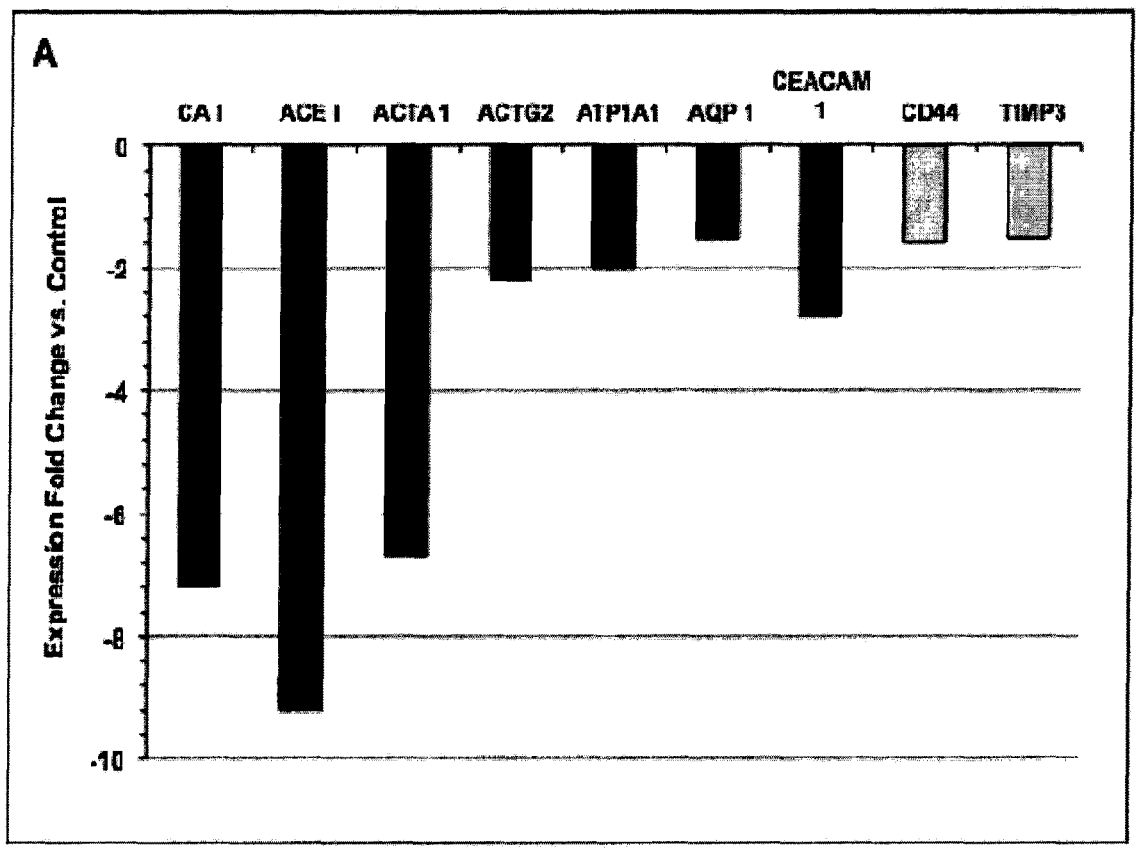
FIG. 10A shows genes down-regulated by 1,25-$(OH)2D3$: CA I, carbonic anhydrase I; ACE, angiotensin 1-converting enzyme; ACTA1, actin alpha 1; ACTG2, actin gamma 2; ATP1A1, Na+/K+ transporting ATPase, alpha 1 polypeptide; AQP1, aquaporin 1; CEACAM1, CEA-related cell adhesion molecule 1; FN1, fibronectin 1; CD44, Hyaluronate receptor or cell adhesion molecule (CD44) and TIMP3, tissue inhibitor of metalloproteinases 3.
Figure 10B:
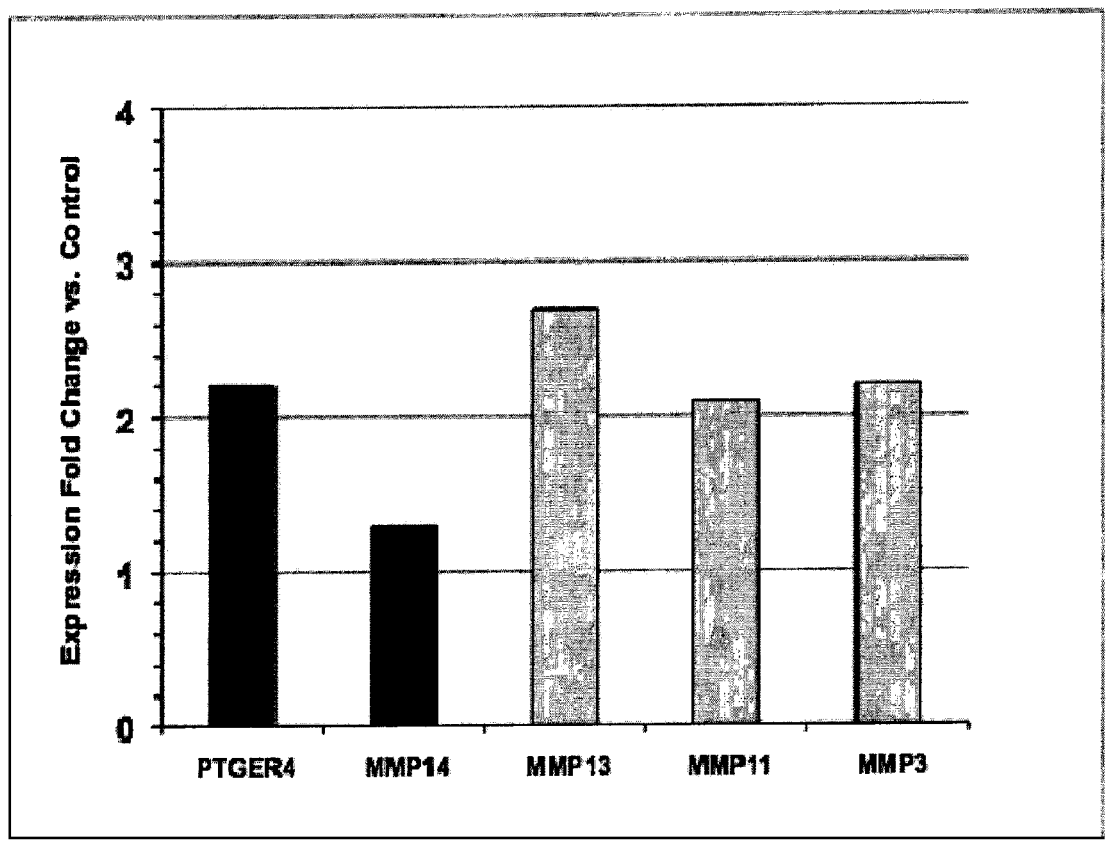
FIG. 10B shows genes up-regulated by 1,25-$(OH)2D3$: PGER4, prostaglandin E receptor subtype 4; MMP3, MMP11, MMP13, MMP14, matrix metalloproteinases 3, 11, 13, 14. The fold change is the average of 2-3 microarray experiments.

We used rat and mouse microarrays for identification of a novel vitamin D target genes that we selected as described in [Kutuzova, 2004]. Comprehensive microarray data analysis showed that 1,25-dihydroxyvitamin D$_3$ (1,25-(OH)$_2$D$_3$) altered expression of genes known to be involved in the regulation of IOP. The largest relevant changes found included strong reductions in mRNA expression for carbonic anhydrase I (CAI), angiotensin I converting enzyme (ACE) and actin alpha (ACTA1) (FIG. 10A). Significantly down-regulated by 1,25-(OH)$_2$D$_3$ were actin gamma (ACTG2), Na+/K+ ATPase alpha 1 (ATP1A1), aquaporins 1 (AQP1), carcinoembryonic antigen-related cell adhesion molecule 1 (CEACAM), fibronectin 1 (FN1), CD44 and tissue inhibitor of metalloproteinase 3 (TIMP3) (FIG. 10A). Significant increases were found in the expression of prostaglandin E receptor 4 for PGE2 (PTGER4) and matrix metalloproteinases 3 (MMP3), 11 (MMP11) and 13 (MMP13) (FIG. 10B). In our study, vitamin D decreased expression of several other genes (vasoactive intestinal peptide, topoisomerase I, MMP2) (the data are not shown) that were found consistently up-regulated in the human trabecular meshwork (TM) during a pressure-induced homeostatic response [Vittitow, 2004].

Topical Application of 1α,25-Dihydroxyvitamin D3 Strongly Reduces IOP in Nonhuman Primates Bilaterally.

Figure 11A:
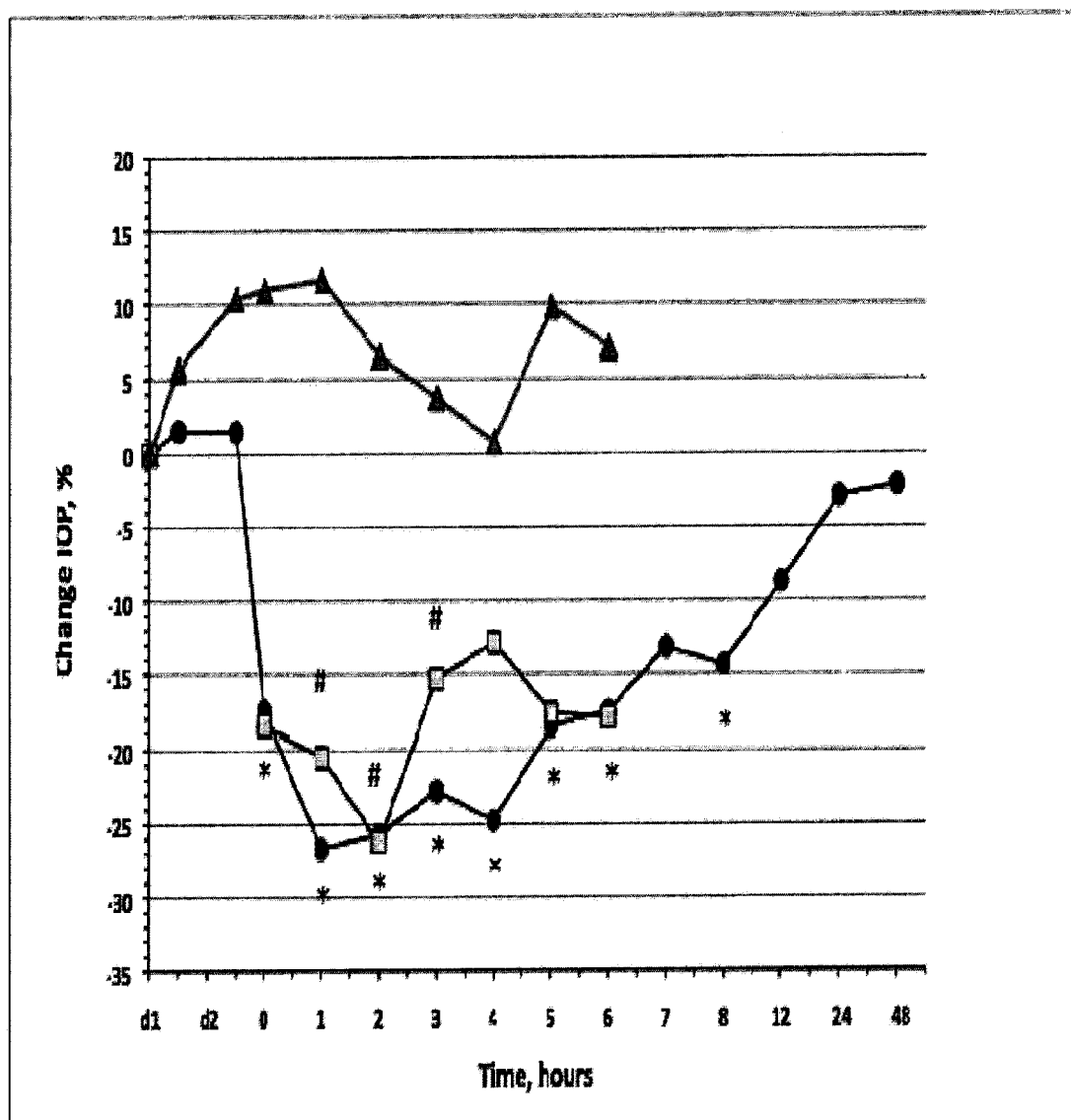
FIG. 11 depicts IOP-changes, % (mean±SEM) in (A) Control (vehicle, 5 μl propylene glycol) and (B) vitamin D (1,25-$(OH)_2D_3$ in 5 μl of propylene glycol) treated eyes of normotensive cynomolgus monkeys after unilateral topical administration of 0.1 μg (triangles, n=7); 1 μg (squares, n=7) and 5 μg (circles, n=8) 1,25-$(OH)_2D_3$ (see Example 3). Pretreatment IOP on day 1 (d1) (mean±SEM) was 17.5±0.5 in to-be-0.1 μl vitamin D-treated eyes and 17.0±0.5 in to-be-control eyes; 19±0.9 in to-be-1 μg vitamin D-treated eyes and 20.0±0.9 in to-be-control eyes; 18.9±0.7 mmHg in to-be-5 μg vitamin D-treated eyes 18.5±0.9 mmHg in to-be-control eyes. (#), (*) Significantly different from respective day one baseline for 1 μg or 5 μg respectively 1,25-$(OH)_2D_3$ treatment experiment by the two-tailed paired t-test (p<0.05). d=day.
Figure 11B:
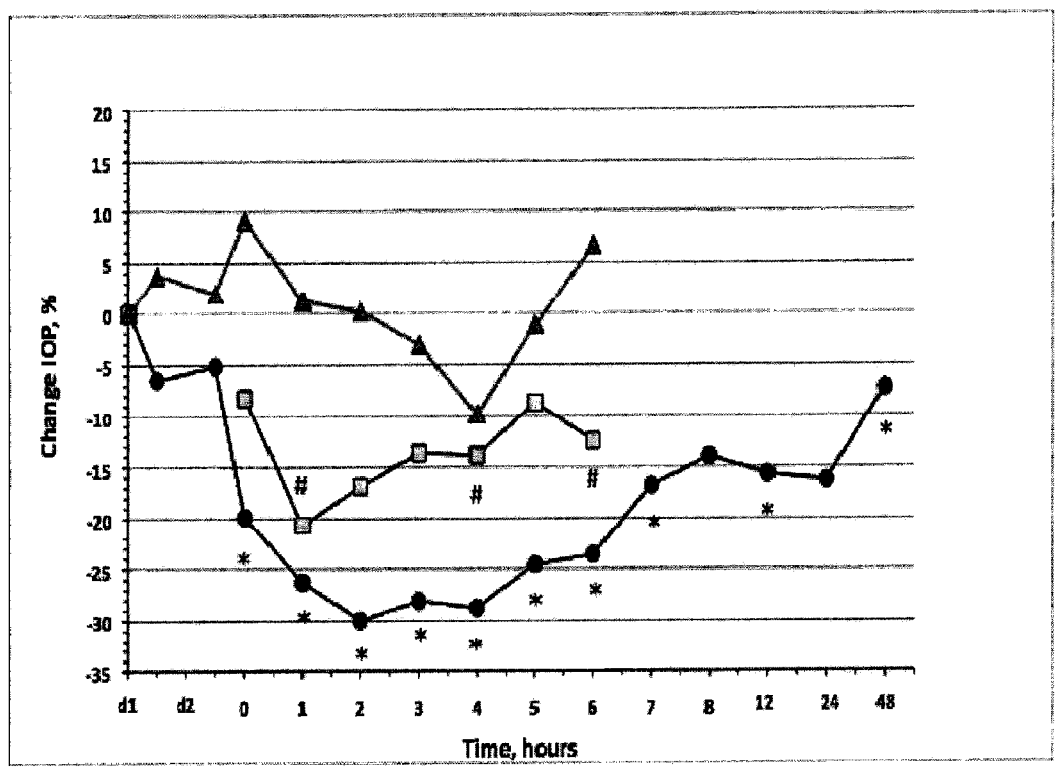

Pretreatment IOP on day 1 (d1) (mean±SEM) was 18.9±0.7 mmHg in eyes to-be-treated with 5 µg of vitamin D and 18.5±0.9 mmHg in to-be-control eyes. Prior to the fifth treatment on day 3 (d3), IOP had significantly decreased by approximately 20% (3 mmHg) in both eyes (p<0.05) (FIG. 11A, B). Following the fifth topical treatment with vitamin D compound of the present invention or vehicle, IOP decreased bilaterally by an additional 7% (1.5 mmHg) in control eyes and by 10% (2.5 mmHg) in vitamin D treated eyes over the next 1-4 hours before gradually returning to near pretreatment baseline after 48 hours (FIG. 11). There appeared to be a slightly greater IOP reduction in the 5 µg vitamin D treated eye as compared to the control eyes (30% vs. 27%) but there were no significant differences between the two eyes except for the time period of 12 h or longer (FIG. 11). In a separate experiment, the vehicle (propylene glycol) alone with no treatment of the contralateral eye had little or no effect on IOP (data not shown).

The IOP Reduction by Vitamin D was Dose-Dependent.

Unilateral topical treatment with 1 µg of vitamin D decreased IOP bilaterally but to a lesser extent than treatment with 5 µg of 1,25-(OH)$_2$D$_3$ (20% vs. 30%) with stronger IOP reduction in the fellow control eyes than in the treated eyes (FIG. 11). Unilateral 0.1 µg of 1,25-(OH)$_2$D$_3$ did not have any significant effect on IOP in either eyes (FIG. 11).

Vitamin D does not Change the Serum Calcium Level in Monkeys.

Since vitamin D functions to maintain blood serum calcium level [DeLuca, 2008], we monitored the serum calcium levels in monkeys as the indicator of whether or not the topically applied vitamin D reaches the sufficient levels to produce the systemic effects. In monkeys treated for 3 days with 5 µg of 1,25-(OH)$_2$D$_3$ (total 5 topical applications) by unilateral topical application in one eye, blood serum calcium levels did not change (FIG. 6) indicating that 1,25-(OH)$_2$D$_3$ did not enter the systemic circulation in sufficient levels to cause systemic effects characterized by the elevation of blood serum calcium level.

Vitamin D has No Effect on the Aqueous Humor Dynamics in Monkeys.

There were no changes in the aqueous humor formation rates in vehicle control or in 5 µg vitamin D treated eyes compared to the baseline or to each other post treatment at any time interval when IOP was strongly decreased bilaterally (Table 1, FIG. 11).

TABLE 1

Aqueous humor formation (AHF) (µl/min) in eyes of cynomolgus monkeys after topical application of 5 µg vitamin D (1,25-(OH)$_2$D$_3$) or vehicle (propylene glycol).

|  | Vitamin D | Vehicle | Vitamin D/Vehicle |
| --- | --- | --- | --- |
| Hours 1-6 |  |  |  |
| Baseline | 1.36 ± 0.11 | 1.46 ± 0.08 | 0.93 ± 0.06 |
| Vitamin D | 1.53 ± 0.10 | 1.52 ± 0.10 | 1.01 ± 0.07 |
| Rx/Baseline | 1.14 ± 0.06 | 1.05 ± 0.06 | 1.10 ± 0.07 |
| Hours 1-3 |  |  |  |
| Baseline | 1.36 ± 0.22 | 1.40 ± 0.14 | 0.95 ± 0.08 |
| Vitamin D | 1.27 ± 0.08 | 1.37 ± 0.08 | 0.94 ± 0.05 |
| Rx/Baseline | 1.06 ± 0.10 | 0.99 ± 0.08 | 1.07 ± 0.06 |
| Hours 4-6 |  |  |  |
| Baseline | 1.24 ± 0.11 | 1.51 ± 0.16 | 0.85 ± 0.08 |
| Vitamin D | 1.54 ± 0.14 | 1.58 ± 0.06 | 0.98 ± 0.10 |
| Rx/Baseline | 1.25 ± 0.09 | 1.10 ± 0.13 | 1.22 ± 0.16 |

Aqueous humor formation was measured by fluorophotometry during the interval 1-6 hr after the 5th topical bid treatment with vitamin D or vehicle to opposite eyes (see Materials and Methods). Units for aqueous humor formation are µl/min. Data are Mean±Sem. Rx, treatment (Vitamin D or vehicle) n=6.

Baseline outflow facilities were studied in two groups (A and B) of monkeys (Materials and Methods). Group A (n=4) was treated with single bolus intracameral injection of 1 µg vitamin D (1,25-(OH)$_2$D$_3$) in 1 µl propylene glycol in one eye and 1 µl vehicle, propylene glycol in the control eye (Table 2, A). Group B (n=4) was treated topically with 5 µg of vitamin D in 5 µl of propylene glycol or vehicle (5 µl of propylene glycol) twice daily for two days. Then, following baseline outflow facility measurements on the third day, the fifth treatment was administered as a single bolus injection of 1 µl of 1 µg vitamin D 1,25-dihydroxyvitamin D$_3$ (1,25-(OH)$_2$D$_3$) into the anterior chamber of one eye (Treated eye) or 1 µl of propylene glycol into the anterior chamber of fellow eye (Control eye).

TABLE 2

Cumulative 90 min outflow facility in monkey eyes after topical and/or intracameral application of vitamin D (1,25-(OH)$_2$D$_3$) (Treated eye) or vehicle (propylene glycol) (Control eye).

|  | Outflow facility (µl/min/mmHg) | | Ratios |
| --- | --- | --- | --- |
|  | Treated eye | Control eye | Treated/Control |
| Group A. 1 µg Intracameral (n = 4) |  |  |  |
| Baseline | 0.24 ± 0.08 | 0.29 ± 0.07 | 0.90 ± 0.34 |
| Vitamin D | 0.37 ± 0.07 | 0.47 ± 0.05 | 0.82 ± 0.20 |
| Vitamin D/Baseline | 1.80 ± 0.30 | 1.79 ± 0.30 | 1.04 ± 0.13 |
| Group B. 5 µg Topical (4 treatments); 1 µg Intracameral (n = 4) |  |  |  |
| Baseline | 0.31 ± 0.12 | 0.38 ± 0.23 | 1.11 ± 0.17 |
| Vitamin D | 0.51 ± 0.26 | 0.68 ± 0.43 | 0.91 ± 0.27 |
| Vitamin D/Baseline Combined Data for Groups A and B | 1.39 ± 0.45 | 1.74 ± 0.39 | 0.84 ± 0.18 |

TABLE 2-continued

Cumulative 90 min outflow facility in monkey eyes after topical and/or intracameral application of vitamin D (1,25-(OH)$_2$D$_3$) (Treated eye) or vehicle (propylene glycol) (Control eye).

| | Outflow facility (µl/min/mmHg) | | Ratios |
|---|---|---|---|
| | Treated eye | Control eye | Treated/Control |
| (n = 8) | | | |
| Baseline | 0.28 ± 0.07 | 0.34 ± 0.11 | 1.00 ± 0.18 |
| Vitamin D | 0.44 ± 0.13 | 0.58 ± 0.20 | 0.87 ± 0.16 |
| Vitamin D/Baseline | 1.59 ± 0.19* | 1.77 ± 0.16* | 0.94 ± 0.11 |

Data are Mean ± SEM.
Outflow facility units are µl/min/mmHg;
ratios are unitless.
Following baseline measurements, intracameral 1 µg of vitamin D was administered to one eye; vehicle (1 µl) to the opposite eye.
Outflow facility measurement post treatment were begun 75 minutes after Vitamin D administration and continued for 90 minutes.
Topical administration of 5 µg of vitamin D or vehicle for 2 days (4 treatments) with intracameral treatment same as in Group A on the third day (see Materials and Methods for details).
No significant difference was found between eyes when the data for the entire 90 minutes period was analyzed or when 30 minutes increments were analyzed. Significantly different from 1.0 by the two-tailed paired t-test: *p < 0.05.

We compared the cumulative 90 min outflow facilities between vitamin D or vehicle treated eyes in each treatment groups A and B (Table 2) and compared them to baseline facilities. There was increase in outflow facilities for entire 90 min period for both eyes in each treatment group, but no significant differences were found neither between the vitamin D or vehicle treated eyes (Table 2) nor between both groups or when we combined data for both groups (Table 2). Also no significant difference was found between eyes when the data for the entire 90 minutes period was analyzed or when 30 minutes increments were analyzed.

Figure 12:
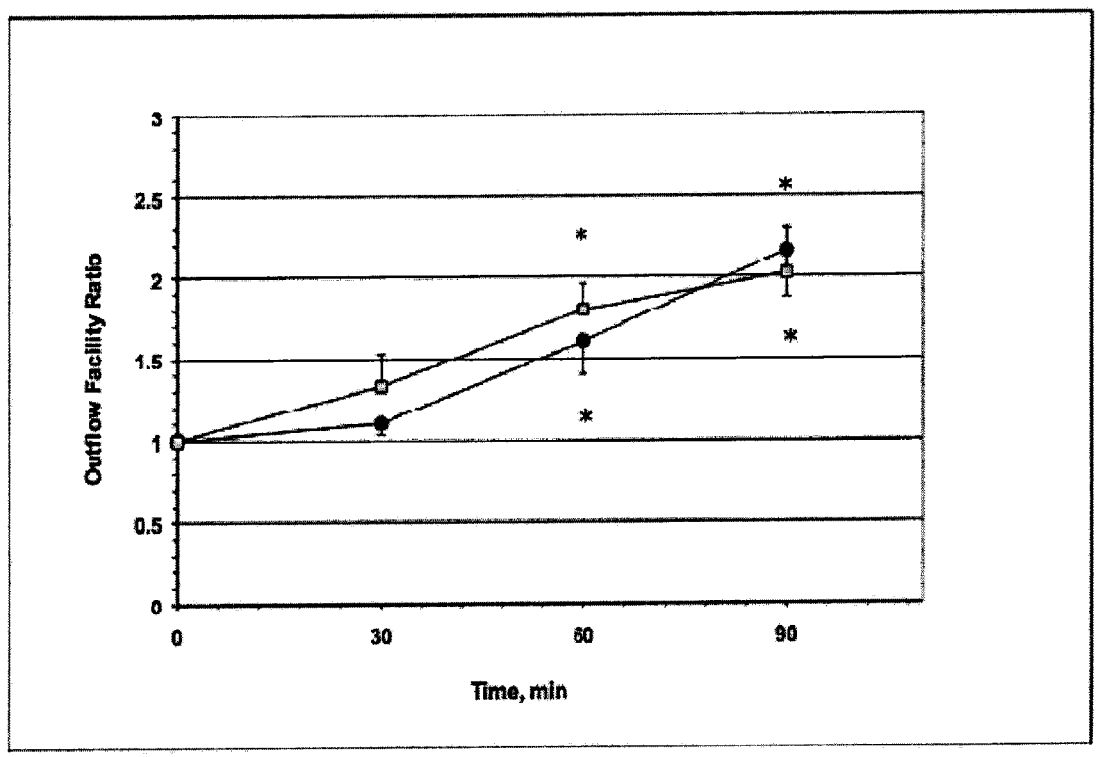
FIG. 12 depicts outflow facility ratios plotted against time (Mean±SEM, n=8, combined groups A and B, see Table 2) measured within 30 min intervals (normalized with respect to an initial 90 min baseline). Open squares correspond to perfusion with vehicle (propylene glycol) in Control eye and solid dots correspond to perfusion with vitamin D (1,25-$(OH)_2D_3$ in propylene glycol) in contralateral eye of normotensive cynomolgus monkeys (see Example 3). No significant difference was found between eyes when the data for the entire 90 minutes period was analyzed or when 30 minutes increments were analyzed. Significantly different from 1.0 by the two-tailed paired t-test: *p<0.05.

For the time course of outflow facilities ratios (as 30 min intervals) the results of both groups of monkeys were combined (n=8) since there was no obvious difference in the responses (Table 2, FIG. 12). There was a slight non-significant increase in outflow facilities in both eyes during the first 30 min after the bolus injection (33% in control eyes, 10% in vitamin D treated eyes) (FIG. 12) followed by a significant increase of 80-60% at 60 min and 100-115% at 90 min in both vehicle and vitamin D treated eyes respectively (FIG. 12). Since outflow facilities in both eyes (vitamin D and vehicle treated) were increased over the baseline to the same moderate extent (about 100% at 90 min after the intracameral injections), similar to what was described in [Rasmussen, 2007] we consider these bilateral outflow facilities increase as simply the "washout" phenomenon known to occur in all non-human species [Scott, 2007]. Still there might be some probability that it was due to a true bilateral outflow facility increase, which stimulated the strong bilateral IOP reduction by vitamin D we discovered (FIG. 12). Additional experiments to provide insight as to whether or not uveoscleral outflow may be involved in the IOP—lowering effect of vitamin D are warranted. Due to the bilateral nature of the IOP response, the most promising approach would involve constricting the ciliary muscle with pilocarpine to block the uveoscleral outflow pathway [Crawford, 1987] prior to vitamin D treatment.

Discussion.

Previously, microarray studies identified numerous novel vitamin D target genes in rat intestine involved in Ca$^{2+}$ absorption and immunomodulation suggesting a novel pathway for vitamin D-induced Ca$^{2+}$ absorption [Kutuzova, 2004]. The comprehensive microarray data analysis in rats and mice presented herein shows the novel vitamin D-modulated genes that are known to be involved in the regulation of IOP. Many changes in gene expression that we observed after the vitamin D treatment are relevant to the regulation of aqueous humor formation and drainage. Our microarray studies also show that vitamin D modulated expression of genes may negate the events associated with dexamethasone treatment of trabecular meshwork cells, thereby providing a treatment for steroid-induced glaucoma in susceptible individuals [Rozsa, 2006].

In addition to the microarray studies mentioned above, we investigated the effect of vitamin D on IOP, aqueous humor formation and outflow facility in nonhuman primates following topical and/or intracameral administration.

It has long been suggested that extracellular matrix (ECM) components of the ocular drainage pathways are crucial determinants of resistance to aqueous humor outflow and consequently of the IOP [Kaufman, 1984]. ECM molecules and factors that affect their metabolism, synthesis, and response to changing environments are important components of susceptibility to ocular hypertension. Enhancing trabecular outflow can be achieved by disrupting the actin cytoskeleton. Compounds with cytoskeletal effects offer therapeutic possibilities for substantial long-term IOP reduction. Most current IOP-reducing agents either suppress aqueous humor production or increase outflow through the ciliary muscle, thus reducing aqueous humor flow through the TM. All currently known IOP lowering agents have more or less severe side effects [Kaufman, 2006].

Conventional treatments for lowering IOP, such as BETA-GAN® (levobunolol) or XALATAN® (latanoprost), can cause side effects including transient ocular burning and stinging, blepharoconjunctivitis, decreases in heart rate and blood pressure, iridocyclitis, headache, transient ataxia, dizziness, lethargy, urticaria, macular edema, pruritus, a decreased corneal sensitivity, upper respiratory tract infections/flu and/or a rash or allergic reactions. None of these side effects have been seen in the compounds of the present invention.

Vitamin D is able to prevent and cure a broad spectrum of diseases such as rickets, cancers, diabetes and autoimmune diseases [DeLuca, 2004, 2008]. Another biological function of vitamin D is to regulate genes responsible for detoxification of endo- and xenobiotics [Kutuzova, 2007]. The active form of vitamin D is 1,25 dihydroxyvitamin D$_3$ or calcitriol (1,25(OH)$_2$D$_3$), a seco-steroid hormone, that in association with high affinity vitamin D receptor (VDR) and following heterodimerization with the retinoid X receptor acts as a ligand-activated transcription factor and binds to specific DNA—vitamin D response elements (VDREs), transactivating or transrepressing a large variety of genes [Jones, 1998]. From our microarray study in rats (in vivo) [Kutuzova, 2004] and mice (in vitro) treated with the active form of vitamin D (1,25(OH)$_2$D$_3$) we discovered that vitamin D-modulated genes of the cell cytoskeleton, extracellular matrix, cell adhesion and genes of other proteins and enzymes that are known to be involved in IOP regulation (FIG. 10).

Cytoskeleton dynamics has been implicated in trabecular meshwork function and aqueous humour outflow regulation since actin-depolymerizing drugs increased outflow facility and decreased IOP. Agents, which disrupt the actin cytoskeleton lower IOP and increase outflow facility in vivo. We show here for the first time that vitamin D strongly down-regulates the expression of the major cytoskeleton proteins (actins, alpha and gamma), decreases expression of proteins involved in cell adhesion (CEACAM and CD44) and fibronectin I—one of the major ECM proteins involved in ECM organization and cell interaction (FIG. 10A). Actin disruptions can lead to alterations in cellular adhesions resulting in relaxation of the trabecular meshwork to enhance the area available for fluid outflow [Tian, 2008]. CEACAM has not been investigated in the outflow pathways but reductions in cell adhesion molecules in general would be expected to enhance outflow through the trabecular meshwork [Kuespert, 2006]. Reductions in fibronectin 1 and in CD44 that we observed after the vitamin D treatment might also lead to enhanced fluid outflow by decreasing the outflow resistance as the result of disruption of the cellular adhesions and reductions in contractility molecules [Wordinger, 2007; Acott, 2008; Tan, 2006].

Vitamin D increased expression of matrix metalloproteinases (FIG. 10B) and decreased expression of their inhibitors (FIG. 10A). Matrix metalloproteinases (MMPs) and their inhibitors remodel ECM material. Elevated levels of matrix metalloproteinases can remodel the extracellular matrix resulting in enhancement of fluid outflow and in the reduction of IOP [Tan, 2006].

The other class of genes down-regulated by vitamin D that we present here for the first time, and which are also known to be involved in IOP reduction, are transporters and channels: aquaporin 1 (Aqp1) and sodium-potassium ATPase (ATP1A1) (FIG. 10A). Aqp1 is the water channel and is expressed at sites of aqueous fluid production and outflow. Mice deficient in aquaporin water channel genes have lower aqueous humor inflow and lower IOP than normal controls [Zhang, 2002]. Therefore, inhibiting aquaporins could be utilized for glaucoma therapy. ATP1A1 in the non-pigmented ciliary epithelium is involved in aqueous humor formation [Riley, 1986]. Inhibiting the ciliary process ATP1A1 by cardiac glycosides (e.g. ouabain) or vanadate significantly reduces the rate of aqueous humor formation and IOP in experimental animals [Podos, 1984; Dismuke, 2009] and humans [Podos, 1989].

Previously [Kutuzova, 2004] we identified other genes whose expression was drastically suppressed by vitamin D and that are relevant to IOP reduction including angiotensin I converting enzyme (ACE) and carbonic anhydrase (CAI) (FIG. 10A). Carbonic anyhydrase inhibitors are widely employed for glaucoma therapy to lower IOP by suppressing aqueous humor formation [Mincione, 2007; Supuran, 2008].

ACE is known to be a key part of the renin angiotensin system that regulates blood pressure by converting angiotensin I (AngI) to angiotensin II (AngII), which then increases vasopressin release. ACE can also inactivate the vasodilatator bradykinin. Both of these effects elevate arterial blood pressure. ACE inhibitors are widely used for the treatment of hypertension. There also is evidence that the eye contains a renin-angiotensin system and that it may be involved in the regulation of IOP. The presence of ACE activity, the concentrations of angiotensinogen and angiotensin II, and the density of angiotensin-II AT1 receptors in ocular tissues and fluids have been demonstrated in several species, including humans [Wallow, 1993; Cullinane, 2002; Vaajanen, 2008]. The recent studies in hypertensive rats suggested the strong positive correlation between the blood pressure and IOP [Vaajanen, 2008].

A strong correlation between blood pressure and IOP was established also in a human comprehensive study suggesting a common mechanism or common genes that may be controlling pressure both in the eye and in the vascular system [Klein, 2005; Duggal, 2007]. Topical and oral administration of ACE inhibitors has been shown to lower IOP in animal models and in humans; they are currently under development as glaucoma therapeutic agents [Constad, 1988; Costagliola, 1995]. Epidemiological and clinical studies of many years established an inverse relationship between vitamin D and blood pressure in human population (Li, Y. C., 2003). Vitamin D is a potent suppressor of the renin-angiotensin system and can reduce blood pressure [Li, 2004]. The strong inhibition of ACE expression by vitamin D described previously [Kutuzova, 2004] could be one of many genetic factors responsible for the vitamin D lowering effect of both arterial blood pressure and IOP.

The significant vitamin D induced increase in the expression of prostaglandin E receptor 4 (EP4) for prostaglandin E2 (FIG. 10B) could also contribute to IOP reduction, since ocular hypotensive effect of prostaglandin E2 (PGE2) analogs is mediated by multiple EP receptors present in the eye [Takamatsu, 2000]. Prostaglandins induce matrix metalloproteinases that degrade the ECM in the TM to enhance outflow. Therefore the increased expression of the EP4 receptor stimulated by vitamin D could also contribute to IOP reduction.

The current study demonstrates that topically applied vitamin D indeed is able to substantially lower IOP in non-human primates and thus vitamin D and the whole class of its compounds have the potential to be used as glaucoma therapeutics. The only known previous study supporting the potential use of vitamin D to lower IOP took place more than 50 years ago, when a single intramuscular injection of vitamin $D_2$ (not vitamin $D_3$) was administered to several patients with glaucoma and IOP reduction was observed in some patients [Guist, 1953].

However, these data were not statistically significant, have never been repeated and thus the question on the reproducibility of the results remained open. Moreover vitamin $D_2$ or ergocalciferol, often plant-sourced, is not the endogenous human form of vitamin D (which is vitamin $D_3$) and has far less effect in the body. The other indirect evidence supporting our idea that vitamin D plays the role in IOP regulation and thus in POAG comes from epidemiological studies showing the prevalent susceptibility of African-descent population to POAG as compared to Caucasian populations [Miao, 2008; Lucas, 2008]. Individuals with African ancestry are known to have approximately two-fold lower levels of serum vitamin D (25(OH)D) compared with individuals of European ancestry [Harris, 2006; Zadshir, 2005] due to the fact that pigmentation reduces vitamin D production in the skin. Lower vitamin D status may account for this population being more prone to high blood pressure, diabetes [Harris, 2006] and a higher prevalence of peripheral arterial disease [Reis, 2008].

We showed that IOP is significantly lowered in nonhuman primates following the topical 1,25 dihydroxyvitamin $D_3$ or calcitriol application in a dose-dependent manner with prolonged effects lasting more than 12 hours (FIG. 11). The reduction in IOP occurred bilaterally after unilateral topical application even at lower doses (FIG. 11A). The mechanism of the bilateral IOP decrease by some agents is not clearly understood or explained. One possible mechanism for the contralateral effect is systemic absorption of the topically applied drug through the nasolacrimal mucosa into the blood circulation to the contralateral eye (Piltz, 2000) e.g. detectable plasma levels of the calcium channel blocker flunarizine were reported in rabbits after its topical administration [Maltese, 2003].

Another possibility is that the compound acts through the CNS or peripheral nervous systems [Trzeciakowski, 1987]. Some investigators have emphasized that the nervous system must be considered as the most important regulator of IOP, since changes in IOP were recorded after stimulation of sensory, sympathetic and parasympathetic (both oculomotor and facial) nerve fibers [tenTusscher, 1994]. The cannabioids, opioids and prostaglandins also decrease IOP bilaterally but not to the same extent as vitamin D [Rasmussen, 2007; Kaufman 2008]. $Ca^{2+}$ channel blockers, $\alpha_2$- and β-adrenergic antagonists also cause bilateral IOP decrease, which is usually less prominent in the control eye than in the treated eye [Wang, 2008; Gabelt, 1994; Piltz, 2000]. This suggests that the compounds of the present invention may be useful in treating disorders of the nervous system (CNS/PNS) such as depression, brain cancer, Alzherimer's, Parkinson and the like As the first step in the investigation we studied the aqueous humor formation process. It has became clearly obvious from our experiments that vitamin D does not change the aqueous humor formation (Table 1). Next we studied the aqueous humor outflow facility in vitamin D treated monkey eyes and showed that both vehicle and vitamin D treated eyes experienced the identical increase in outflow facilities (Table 2, FIG. 12). The moderate degree of outflow facility increase, stimulated by vitamin D in both, vehicle and vitamin D treated eyes, is likely the result of "washout" phenomenon common in all species except humans, and in which perfusion of an eye at physiological pressure results in a volume-dependent increase in the measured facility of aqueous humor outflow [Scott, 2007]. Similar results were observed for outflow facilities bilateral increase that was considered as "washout" in monkeys treated with kappa opioid agonist bremazocine [Rasmussen, 2007].

In our study vitamin D did not change either the aqueous humor flow or the outflow facilities and thus did not effect the aqueous humor dynamics in nonhuman primates. This is in stark contrast to all other known ocular hypotensive agents, suggesting that vitamin D's mechanism of lowering IOP may be different from that of other ocular hypotensive agents. Given the variety of vitamin D target genes presented here involved in IOP regulation, there is a strong evidence to suggest that vitamin D has the potential to lower IOP via several mechanisms.

It should be noted that the above description, attached figures and their descriptions are intended to be illustrative and not limiting of this invention. Many themes and variations of this invention will be suggested to one skilled in this and, in light of the disclosure. All such themes and variations are within the contemplation hereof. For instance, while this invention has been described in conjunction with the various exemplary embodiments outlined above, various alternatives, modifications, variations, improvements, and/or substantial equivalents, whether known or that rare or may be presently unforeseen, may become apparent to those having at least ordinary skill in the art. Various changes may be made without departing from the spirit and scope of the invention. Therefore, the invention is intended to embrace all known or later-developed alternatives, modifications, variations, improvements, and/or substantial equivalents of these exemplary embodiments.

REFERENCES

1. Acott T S, Kelley M J. *Exp Eye Res*. (2008) April; 86(4):543-61.
2. Armaly et al. *Arch. Ophthalmol*. (1980), 98:2163-2171.
3. Bárány E H. *Invest Ophthalmol*. (1964) 3:135-143.
4. Chidlow et al. *Exp. Eye Res*. (1999) 69:587-593.
5. Chu et al. *J. Phamracology and Experimental Therapeutics*. (2000) 293:710-716.
6. Clark A F, Yorio T. *Nat Rev Drug Discov*. (2003) June; 2(6):448-59.
7. Constad et al. *Am J Ophthalmol*. (1988) 105:674-677.
8. Costagliola et al. Eur J Ophthalmol. (1995)5:19-25.
9. Crawford K, Kaufman P L. *Arch Ophthalmol*. (1987)105: 1112-1116.
10. Croft et al. *Basic and Clinical Applications of Vision Science*. (1997) 60:213-216.
11. Cullinane et al. *Br. J. Ophthalmol*. (2002) 86:676-683.
12. DeLuca H F. *Am. J. Clin. Nutr*. (2004) 80:1689S-1696S.
13. DeLuca H F. *Nutrition Reviews* (2008) 66(Suppl. 2):S73-S87.
14. Dismuke et al. *Br. J. Ophthalmol*. (2009) January; 93(1):104-9.
15. Duggal et al. *Arch. Ophthalmol*. (2007) January; 125 (1):74-9.
16. Ereemeev et al., Pharm. Chem. Journal. (2006) 41 (1): 36-39.
17. Gabelt et al. *Invest Ophthalmol. Vis. Sci*. (2004)45:2732-2736.
18. Gabelt et al. *Exp. Eye Res*. (1994) December; 59(6): 633-44.
19. Guist G, Steffen C. Klin. Monatsbl. Augenheilkd. (1953) 123(5):555-68.
20. Halloran B P, DeLuca H F. *Biochem. Biophys*. (1981) 208; N2, 477-486.
20. Harris. *J. Nutr*. (2006) April; 136(4):1126-9.
21. Holick M F. *Mol. Aspects Med*. (2008) December; 29(6):361-8.
21. Institute NE. *National Plan for Eye and Vision Research*.
22. Ontoso et al. *European Journal of Epidemiology*, (1997) January; 13(1):19-23.
23. Jones et al. *Physiological Reviews*. (1998) 78:1193-1231.
24. Kanner E, Tsai J C. *Drugs Aging* (2006) 23(4):321-332.
25. Kass et al. *Arch. Ophthalmol*. (2002) 120:701-713.
26. Kaufman P L. *Curr. Top. Eye Res*. (1984) 4:97-138.
27. Kaufman P L. *Exp. Eye Res*. (2008) January; 86(1):3-17.
28. Kaufman P L, Davis G E. *Arch Ophthalmol*. (1980) 98:542-546.
29. Kaufman P L, Gabelt B T. *Essentials in Ophthalmology*. (2006).
30. Klein et al. *Br. J. Ophthalmol*. (2005) 89:284-287.
31. Kuespert K, Pils S. *Curr. Opin. Cell. Biol*. (2006)18: 565-571.
32. Kutuzova G D, DeLuca H F. *Arch. Biochem. Biophys*. (2004)432:152-166.
33. Kutuzova G D, DeLuca H F. *Toxicol. Appl. Pharmacol*. (2007)218:37-44.
34. Li. *J. Cell. Biochem*. (2003) Feb. 1; 88(2):327-31.
35. Li et al. *J. Steroid Biochem. Mol. Biol*. (2004)89-90: 387-392.
36. Libby et al. *Annu. Rev. Genomics Hum. Genet*. (2005) Sep. 22; 6:15-44.
37. Lim et al. *Ophthalmology*. (2008) May; 115(5):790-795.
38. Lukas et al. *Genome Biol*. (2008) 9(7):R111.1-R111.19.
39. Maltese A, Bucolo C. *J. Ocul. Pharmacol. Ther*. (2003); 19:171-179.
40. Marquis R E, Whitson J T. *Aging*. (2005); 22(1):1-21.
41. Miao et al. *PLoS ONE*. (2008) Aug. 6; 3(8):e2847.
42. Mincione et al. *Curr. Top Med. Chem*. (2007)7:849-854.
43. National Eye Institute Website: www.nei.nih.gov.
44. Orihashi et al. *Biol. Pharm. Bull*. (2005) January; 28(1):65-8.
45. Piltz et al. *Am. J. Ophthalmol*. (2000) October; 130(4): 441-53.
46. Pintor. *Curr. Opin. Invest. Drugs* (2005) 6:76-80.

47. Podos et al. *Australian & New Zealand J. Ophthalmol.* (1989) 17:129-135.
48. Podos et al. *Invest. Ophthalmol. Vis. Sci.* (1984)25:359-361.
49. Rasmussen et al. *Trans. Am. Ophthalmol. Soc.* (2007); 105:225-38.
50. Reis et al. *Am. J. Clin. Nutr.* (2008) December; 88(6): 1469-77.
51. Riley M V, Kishida K. *Exp. Eye Res.* (1968) 42:559-568.
52. Rozsa et al. *Mol. Vis.* (2006) Feb. 27; 12:125-41.
53. Scott et al. *Exp. Eye Res.* (2007) March; 84(3):435-43.
54. Shevde et al. *Proc. Natl. Acad. Sci. USA.* (2002) Oct. 15; 99(21):13487-91.
55. Suda et al. *J. Nutr.* (1970) 100:1049-1052.
56. Supuran C T. *Nat. Rev. Drug Discov.* (2008) February; 7(2):168-81.
57. Takamatsu et al. *Exp. Eye Res.* (2000) 70:623-628.
58. Tan et al. *Curr. Opin. Ophthalmol.* (2006) April; 17(2): 168-74.
59. T et al. *Doc. Ophthalmol.* (1994); 87(4):291-313.
60. Tian et al. *Exp. Eye Res.* (2008), doi:10.1016/j.exer.2008.08.008 available at www.elsevier.com/locate/yexer
61. Trzeciakowski J P. *J. Ocul. Pharmacol.* (1987) 3(4):367-78.
62. Vaajanen et al. *Ann. Med.* (2008) 40(6):418-27.
63. Vaajanen et al. *Curr. Eye Res.* (2008) April; 33(4):325-32.
64. Vittitow J, Borrás T. *J. Cell. Physiol.* (2004) October; 201(1):126-37.
65. Wallow et al. *Curr. Eye Res.* 12:945-950.
66. Wang et al. *J. Glaucoma.* (2008) January-February; 17(1):73-8.
67. Wordinger et al. *Invest. Ophthalmol. Vis. Sci.* (2007) March; 48(3):1191-2000.
68. Zadshir et al. *Data from the NHANES III, Ethn. Dis.* (2005) S5-97-S5-101.
69. Zhang et al. *J. Gen. Physiol.* (2002) 119:561-569.
70. Zimmerman, Kaufman. *Arch. Ophthalmol.* (1977) 95:601-604.

We claim:

1. A method of reducing ocular hypertension in a human subject, the method comprising topically administering to at least one eye a therapeutically effective amount of a vitamin D compound according to the following formula, wherein the compound is administered in an amount ranging from about 0.2 µg to about 1 mg per day:

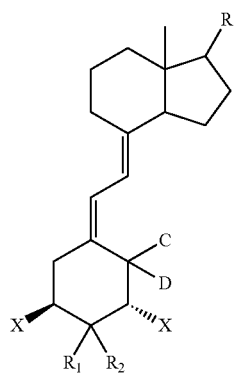

(Formula I)

wherein R is

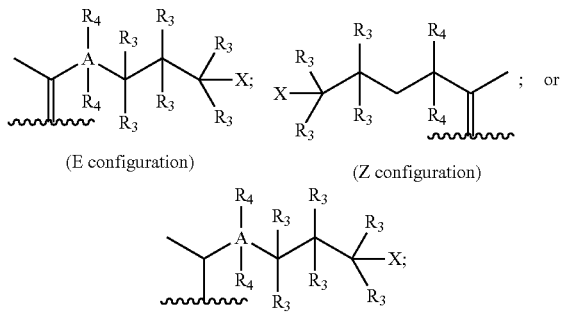

wherein $R_1$ and $R_2$ are H, methyl or 3'-hydroxypropylidine, or taken together as $=CH_2$ or methylene;
wherein $R_3$ and $R_4$ are selected from H, alkyl (1-3 carbons), alkoxy, and can be the same or different from each other;
wherein X is a hydroxyl or protected hydroxyl group;
wherein A is oxygen or carbon, with the proviso that if A is oxygen, then $R_4$ is absent; and
wherein C and D are H or taken together as $=CH_2$; and
wherein the intraocular pressure of the subject is reduced by at least 15%.

2. The method of claim 1 wherein the R is

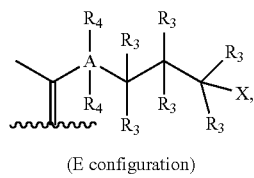

(E configuration)

wherein $R_3$ and $R_4$ are selected from H, alkyl (1-3 carbons), alkoxy, and can be the same or different from each other;
wherein X is a hydroxyl or protected hydroxyl group; and
wherein A is oxygen or carbon, with the proviso that if A is oxygen, then $R_4$ is absent.

3. The method of claim 1 wherein R is

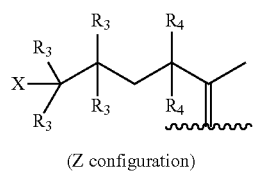

(Z configuration)

wherein $R_3$ and $R_4$ are selected from H, alkyl (1-3 carbons), alkoxy, and can be the same or different from each other; and
wherein X is a hydroxyl or protected hydroxyl group.

4. The method of claim 1 wherein R is

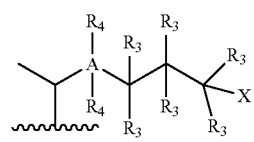

wherein $R_3$ and $R_4$ are selected from H, alkyl (1-3 carbons), alkoxy, and can be the same or different from each other;
wherein X is a hydroxyl or protected hydroxyl group; and
wherein A is oxygen or carbon, with the proviso that if A is oxygen, then $R_4$ is absent.

5. The method of claim 1 wherein the topical preparation is eye drops.

6. The method of claim 1 wherein the vitamin D compound is selected from the group consisting of 1α,25-dihydroxyvitamin $D_3$ (1,25-$(OH)_2D_3$); 2-methylene-19-nor-(20S)-1α,25-dihydroxyvitamin $D_3$; 1α,25-dihydroxy-19-nor-vitamin $D_2$; 2-(3'-hydroxypropylidene)-19-nor-1α,25-dihydroxyvitamin $D_3$ (E-isomer); 17-20 dehydro-2-methylene-19-nor-(20S)-1α,25-dihydroxyvitamin $D_3$ (E- and Z-isomers); 26-homo-1α,25-dihydroxyvitamin $D_3$, 26,27-Dimethyl-1α,25-dihydroxyvitamin $D_3$, 25-hydroxyvitamin $D_3$.

7. A method of reducing intraocular pressure in a human subject's eyes, the method comprising the steps of:
a) determining a baseline intraocular pressure of a first eye;
b) determining a baseline intraocular pressure of a second eye
b) topically administering to the first and second eye a therapeutically effective amount of a vitamin D compound according to the following formula, wherein the compound is administered in an amount ranging from about 0.2 μg to about 1 mg per day:

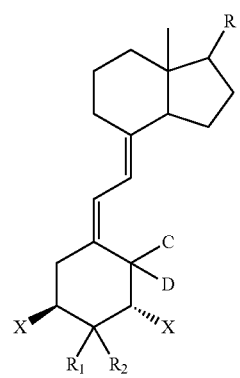

(Formula I)

wherein R is

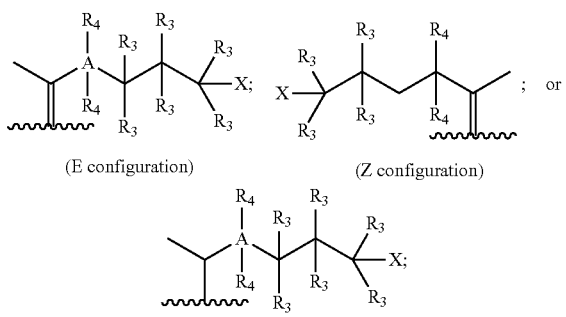

(E configuration)   (Z configuration)

wherein $R_1$ and $R_2$ are H, methyl or 3'-hydroxypropylidine, or taken together as =$CH_2$ or methylene;
wherein $R_3$ and $R_4$ are selected from H, alkyl (1-3 carbons), alkoxy, and can be the same or different from each other;

wherein X is a hydroxyl or protected hydroxyl group;
wherein A is oxygen or carbon, with the proviso that if A is oxygen, then $R_4$ is absent; and
wherein C and D are H or taken together as =$CH_2$; and;
c) measuring the intraocular pressure of the first and second eye;
wherein the ocular hypertension in the first and second eye is reduced by at least 15%.

8. A method of reducing intraocular pressure in a human subject's eyes, the method comprising the steps of:
a) determining a baseline intraocular pressure of a first eye;
b) determining a baseline intraocular pressure of a second eye;
b) topically administering to the first eye a therapeutically effective amount of a vitamin D compound according to the following formula, wherein the compound is administered in an amount ranging from about 0.2 μg to about 1 mg per day:

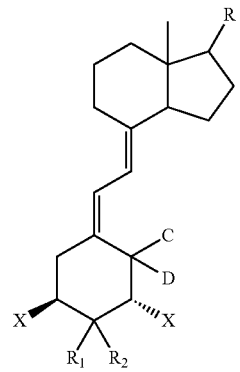

(Formula I)

wherein R is

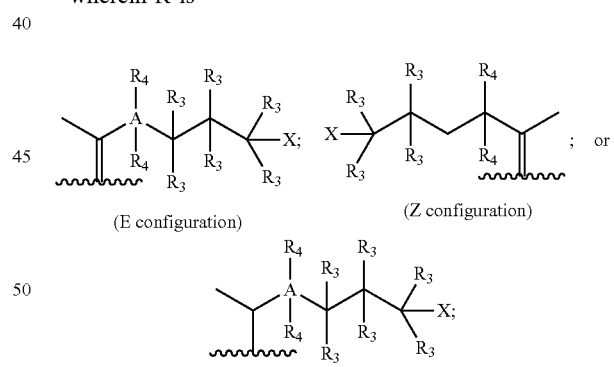

(E configuration)   (Z configuration)

wherein $R_1$ and $R_2$ are H, methyl or 3'-hydroxypropylidine, or taken together as =$CH_2$ or methylene;
wherein $R_3$ and $R_4$ are selected from H, alkyl (1-3 carbons), alkoxy, and can be the same or different from each other;
wherein X is a hydroxyl or protected hydroxyl group;
wherein A is oxygen or carbon, with the proviso that if A is oxygen, then $R_4$ is absent; and
wherein C and D are H or taken together as =$CH_2$; and;
c) measuring the intraocular pressure of the first and second eye;
wherein the ocular hypertension in the first and second eye is reduced by at least 15%.

9. The method of claim 8 wherein the compound is selected from 1α,25-dihydroxyvitamin $D_3$ (1,25-$(OH)_2D_3$); 2-methylene-19-nor-(20S)-1α,25-dihydroxyvitamin $D_3$; 1α,25-dihydroxy-19-nor-vitamin $D_2$; 2-(3'-hydroxypropylidene)-19-nor-1α,25-dihydroxyvitamin $D_3$ (E-isomer); 17-20 dehydro-2-methylene-19-nor-(20S)-1α,25-dihydroxyvitamin $D_3$ (E- and Z-isomers); 26-homo-1α,25-dihydroxyvitamin $D_3$; 26,27-Dimethyl-1α,25-dihydroxyvitamin $D_3$; 25-hydroxyvitamin $D_3$.

* * * * *